(12) United States Patent
Salahieh et al.

(10) Patent No.: US 12,201,804 B2
(45) Date of Patent: Jan. 21, 2025

(54) ENERGY DELIVERY DEVICE AND METHODS OF USE

(71) Applicant: Covidien LP, Mansfield, MA (US)

(72) Inventors: Amr Salahieh, Saratoga, CA (US); Tom Saul, Saratoga, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/351,101

(22) Filed: Jul. 12, 2023

(65) Prior Publication Data

US 2023/0355863 A1 Nov. 9, 2023

Related U.S. Application Data

(60) Division of application No. 17/102,260, filed on Nov. 23, 2020, now abandoned, which is a continuation of
(Continued)

(51) Int. Cl.
*A61M 5/00* (2006.01)
*A61B 18/00* (2006.01)
(Continued)

(52) U.S. Cl.
CPC .......... *A61M 5/007* (2013.01); *A61B 18/1492* (2013.01); *A61M 3/0295* (2013.01); *A61B 2018/00029* (2013.01); *A61B 2018/0022* (2013.01); *A61B 2018/00232* (2013.01); *A61B 2018/0025* (2013.01);
(Continued)

(58) Field of Classification Search
CPC ......... A61M 3/0295; A61B 2018/0022; A61B 2018/00285; A61B 2018/00577; A61B 2018/00744; A61B 2218/002; A61B 2018/00261
See application file for complete search history.

(56) References Cited

U.S. PATENT DOCUMENTS

2005/0059965 A1* 3/2005 Eberl .................... A61M 25/10 606/41
2005/0171527 A1* 8/2005 Bhola ................ A61B 18/1492 606/41
(Continued)

*Primary Examiner* — Serkan Akar
*Assistant Examiner* — Aminah Asghar
(74) *Attorney, Agent, or Firm* — Shumaker & Sieffert, P.A.

(57) ABSTRACT

An energy delivery system for delivering electrical energy to tissue, includes an elongate catheter member defining a longitudinal axis and dimensioned for passage within a body vessel and an expandable treatment member mounted to the catheter member. The treatment member includes an inflatable element adapted to transition between an initial condition and an at least partially expanded condition upon introduction of an anesthetic solution within the inflatable element, an electrode for delivering electrical energy to at least the nerve tissue associated with the body vessel to cause at least partial denervation thereof and at least one aperture dimensioned to permit passage of the anesthetic solution from the inflatable element to contact the body vessel whereby the solution at least enters the body vessel to at least partially anesthetize the nerve tissue therewithin. The electrode may be mounted to at least the inflatable element of the treatment member and may be generally helical.

8 Claims, 16 Drawing Sheets

Related U.S. Application Data application No. 14/391,608, filed as application No. PCT/US2013/032454 on Mar. 15, 2013, now abandoned.

(60) Provisional application No. 61/624,206, filed on Apr. 13, 2012.

(51) Int. Cl.
*A61B 18/14* (2006.01)
*A61M 3/02* (2006.01)
*A61M 25/10* (2013.01)
*A61N 1/32* (2006.01)

(52) U.S. Cl.
CPC .............. *A61B 2018/00255* (2013.01); *A61B 2018/00261* (2013.01); *A61B 2018/00404* (2013.01); *A61B 2018/00434* (2013.01); *A61B 2018/00511* (2013.01); *A61B 2018/00642* (2013.01); *A61B 2018/00708* (2013.01); *A61B 2018/00744* (2013.01); *A61B 2018/00791* (2013.01); *A61B 2218/002* (2013.01); *A61M 2025/105* (2013.01); *A61M 2025/1052* (2013.01); *A61M 2202/048* (2013.01); *A61N 1/327* (2013.01)

(56) References Cited

U.S. PATENT DOCUMENTS

2010/0049192 A1* 2/2010 Holtz ................. A61N 1/36071
606/41
2011/0319809 A1* 12/2011 Smith .................... A61B 5/388
604/21

\* cited by examiner

ENERGY DELIVERY DEVICE AND METHODS OF USE

CROSS REFERENCE TO RELATED APPLICATIONS

The present application is a divisional of U.S. patent application Ser. No. 17/102,260, filed on Nov. 23, 2020, which is a continuation of U.S. patent application Ser. No. 14/391,608, filed on Oct. 9, 2014, now abandoned, which is a U.S. National Stage under 35 U.S.C. § 371 of International Application No. PCT/US2013/032454, filed Mar. 15, 2013, which claims the benefit of, and priority to, U.S. Provisional Application No. 61/624,206 filed on Apr. 13, 2012, the entire contents of each of which are incorporated herein by reference. This application is also related to and incorporates by reference herein the complete disclosures of the following patent applications: U.S. Provisional Pat. App. No. 61/113,228, filed Nov. 11, 2008; U.S. Provisional Pat. App. No. 61/160,204, filed Mar. 13, 2009; U.S. Provisional Pat. App. No. 61/179,654, filed May 19, 2009; U.S. Pat. App. Pub. No. 2010/0204560, filed Nov. 11, 2009; U.S. Provisional Pat. App. No. 61/334,154, filed May 12, 2010; U.S. patent application Ser. No. 13/106,658, filed May 12, 2011; U.S. Provisional Application No. 61/541,756, filed on Sep. 30, 2011; U.S. Provisional Application No. 61/593,147, filed on Jan. 31, 2012; and International Application No. PCT/US12/57967, filed on Sep. 28, 2012.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present disclosure relates generally to medical devices and methods and more particularly to devices and methods for applying radiofrequency energy to tissue.

BACKGROUND

Some medical treatment procedures involve the disruption of a region of tissue. For example, medical treatment procedures include the delivery of energy to disrupt a region of tissue. Radiofrequency ("RF") energy devices are an example of devices that can be used to perform such medical treatments.

Some RF energy devices have a single RF energy element or a plurality of discrete RF energy elements that have to be repeatedly moved within the subject in order to apply sufficient RF energy to the entire region of the tissue. Such RF energy devices may need to be moved within a patient during a given procedure, which can increase the complexity, time, and energy required to perform a given procedure.

SUMMARY

Accordingly, an energy delivery system for delivering electrical energy to tissue, includes an elongate catheter member defining a longitudinal axis and dimensioned for passage within a body vessel, and an expandable treatment member mounted to the catheter member. The treatment member includes an inflatable element adapted to transition between an initial condition and an at least partially expanded condition upon introduction of an anesthetic solution within the inflatable element, an electrode for delivering electrical energy to at least nerve tissue associated with the body vessel to cause at least partial denervation thereof and at least one aperture dimensioned to permit passage of the anesthetic solution from the inflatable element to contact the body vessel whereby the solution enters a wall of the body vessel to at least partially anesthetize the nerve tissue therewithin. The electrode may be mounted to the inflatable element of the treatment member and may be generally helical.

In embodiments, the at least one aperture is dimensioned to deliver the anesthetic solution at a pressure sufficient to facilitate passage of the anesthetic solution at least within the wall of the body vessel. At least one of the inflatable element and the electrode may include a plurality of apertures dimensioned to deliver the anesthetic solution at the pressure sufficient to cause at least passage of the anesthetic solution within the wall of the body vessel. The apertures may be each dimensioned to deliver the anesthetic solution at a pressure ranging from about 1 atm to about 4 atm and, in embodiments, over a flow range of about 1 to about 20 mL/min.

Each aperture may define a pore size ranging from about 0.5 mil to about 10 mil.

In certain embodiments, the catheter member defines a fluid lumen for delivering the anesthetic solution to the inflatable element of the treatment member. A source of anesthetic solution may be in fluid communication with the fluid lumen of the catheter member and the inflatable element of the treatment member. The system further may include a pump couplable to the fluid lumen of the catheter member. The pump may be dimensioned to deliver the anesthetic solution from the source to the fluid lumen of the catheter member at a pressure sufficient to convey the anesthetic lumen through the fluid lumen and out the apertures causing passage of the anesthetic solution at least within the wall of the body vessel. A sensor may be in fluid communication with at least the fluid lumen of the catheter member. The sensor may be a pressure sensor or transducer adapted to sense pressure corresponding to pressure within the inflatable element. In the alternative, the sensor may be a flow rate sensor adapted to detect flow rate associated with passage of the anesthetic solution through the fluid lumen.

In embodiments, the system includes a controller for controlling operation of the pump. The controller may include logic responsive to a parameter detected by the sensor to vary operation of the pump.

In some embodiments, the system includes a source of irrigation fluid in fluid communication with the inflatable element of the treatment member for passage through the apertures for, e.g., cooling the electrode and/or the tissue. The system may further include a valve in fluid communication with the source of anesthetic solution and the source of irrigation fluid. The valve may be actuable between an anesthetic mode to permit the delivery of the anesthetic solution to the fluid lumen of the catheter member and an irrigation mode to permit the delivery of the irrigation fluid to the fluid lumen of the catheter member.

In certain embodiments, the at least one aperture of the treatment member is dimensioned to permit passage of the anesthetic solution at a relatively pressure whereby the anesthetic solution slowly diffuses at least within the body vessel and migrates to the nerve tissue associated with the body vessel. In instances, the inflatable element of the treatment member is dimensioned to establish a reservoir between the inflatable element and a wall of the body vessel when in the at least partially expanded condition thereof. The reservoir receives the anesthetic solution for diffusion through the wall of the body vessel.

The treatment member may include at least one occluding element. The at least one occluding element may define a dimension greater than a corresponding dimension of the inflatable element when the at least one inflatable element is in an at least partially expanded condition thereof. The at least one occluding element may be dimensioned to at least partially occlude the body vessel to at least partially enclose the reservoir.

In some embodiments, the inflatable element is a balloon member. The balloon member includes first and second axially spaced occluding segments and a central segment between the first and second occluding segments. Each of the first and second occluding segments has a transverse dimension greater than a corresponding transverse dimension of the central segment when the balloon member is in a first inflated condition, and dimensioned to substantially occlude the body vessel to enclose the reservoir. The balloon member may be adapted to transition between the first inflated condition and a second inflated condition where the central segment defines a greater transverse dimension to position the electrode in opposition to the body vessel to deliver electrical energy to the nerve tissue associated with and/or surrounding the body vessel. The catheter member may define a fluid lumen for delivering the anesthetic solution to the balloon member.

In other embodiments, the catheter member includes first and second occluding elements mounted adjacent opposed ends of the inflation element. The first and second occluding elements may be adapted to expand to occlude the body vessel and enclose the reservoir established between the inflatable element and the wall of the body vessel. The first and second occluding elements may be adapted for expansion independent of expansion of the inflatable element. The first and second occluding elements may be first and second occluding balloon members and the inflation element may be a treatment balloon member having the electrode mounted thereto. The catheter member may define a second fluid lumen for delivering fluid to the first and second occluding balloon members. As an alternative, the first and second occluding balloon members may be inflatable independent of each other.

In some embodiments, the treatment member includes a first balloon member and a second balloon member coaxially mounted about the first balloon member. The first and second balloon members are dimensioned to establish a reservoir between the first and second balloon members when in the at least partially inflated condition thereof. The reservoir receives the anesthetic solution and the second balloon member may include the at least one aperture dimensioned to permit passage of the anesthetic solution. The first and second balloon members may be inflatable independent of each other. The elongate member may define a second lumen for supplying fluids to the first balloon member to inflate the first balloon member.

In accordance with an aspect of the disclosure, a method for treating hypertension, includes positioning a treatment member including an inflatable segment and an electrode segment within a renal artery; delivering an anesthetic solution into the inflatable segment such that the anesthetic solution is released from at least one aperture of the treatment member to contact a wall of the renal artery whereby the anesthetic solution enters the wall of the renal artery and migrates to renal nerve tissue associated with the renal artery; and emitting RF energy from the electrode segment to disrupt renal nerve transmission to treat hypertension.

In some embodiments, delivering the anesthetic solution includes directing the anesthetic solution to target nerve tissue for alleviating pain during renal denervation. The targeted nerve tissue may include nerve tissue in the intima, media, adventitia, and/or surrounding tissue of a renal artery. The delivery of the anesthetic solution is at a pressure sufficient to enter and/or pass through the wall of the renal artery and contact the desired renal nerve tissue, and may further include directing the anesthetic solution through a plurality of apertures in the treatment member at, e.g., a pressure ranging from about 1 atm to about 4 atm.

In certain embodiments, delivering the anesthetic solution includes permitting passage of the anesthetic solution at a pressure whereby the anesthetic solution slowly diffuses through the wall of the renal artery and possibly migrates to the renal nerve tissue surrounding the renal artery. Delivering the anesthetic solution may include distributing the anesthetic solution within a reservoir defined between the inflatable segment and the wall of the renal artery. In one aspect, the treatment member may include occluding segments adjacent each end of the inflation segment. The occluding segments may be expanded to contact the wall of the renal artery to occlude the artery and substantially enclose the reservoir.

DETAILED DESCRIPTION

Figure 1A:
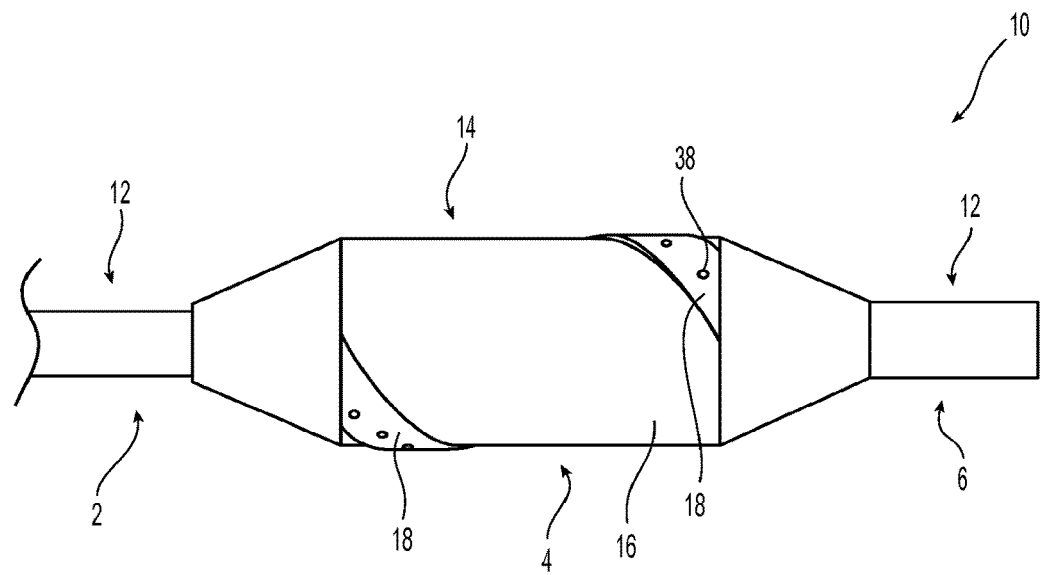
FIGS. 1A, 1B, and 2 illustrate a portion of an energy delivery device comprising a helical electrode on an expandable element according to an embodiment of the present disclosure.

Particular embodiments of the present disclosure are described hereinbelow with reference to the accompanying drawings; however, the disclosed embodiments are merely examples of the disclosure and may be embodied in various forms. Like reference numerals may refer to similar or identical elements throughout the description of the figures.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As used herein, the terms proximal and distal refer to a direction or a position along a longitudinal axis of a catheter or medical instrument. The term "proximal" refers to the end of the catheter or medical instrument closer to the operator, while the term "distal" refers to the end of the catheter or medical instrument closer to the patient. For example, a first point is proximal to a second point if it is closer to the operator end of the catheter or medical instrument than the second point. The measurement term "French", abbreviated Fr or F, is defined as three times the diameter of a device as measured in mm. Thus, a 3 mm diameter catheter is 9 French in diameter. The term "clinician" refers to any medical professional (i.e., doctor, surgeon, nurse, or the like) performing a medical procedure.

One aspect of the disclosure is a RF delivery device that is adapted to deliver RF energy to tissue. FIG. 1A illustrates a side view of a distal region of RF delivery device 10. Device 10 has proximal region 2, intermediate region 4, and distal region 6. Device 10 includes an elongate portion 12 and expandable portion 14 (shown in an expanded configuration) disposed on a distal region of elongate portion 12. Expandable portion 14 includes inflatable element 16 on which conductive material 18 is disposed.

Figure 1B:
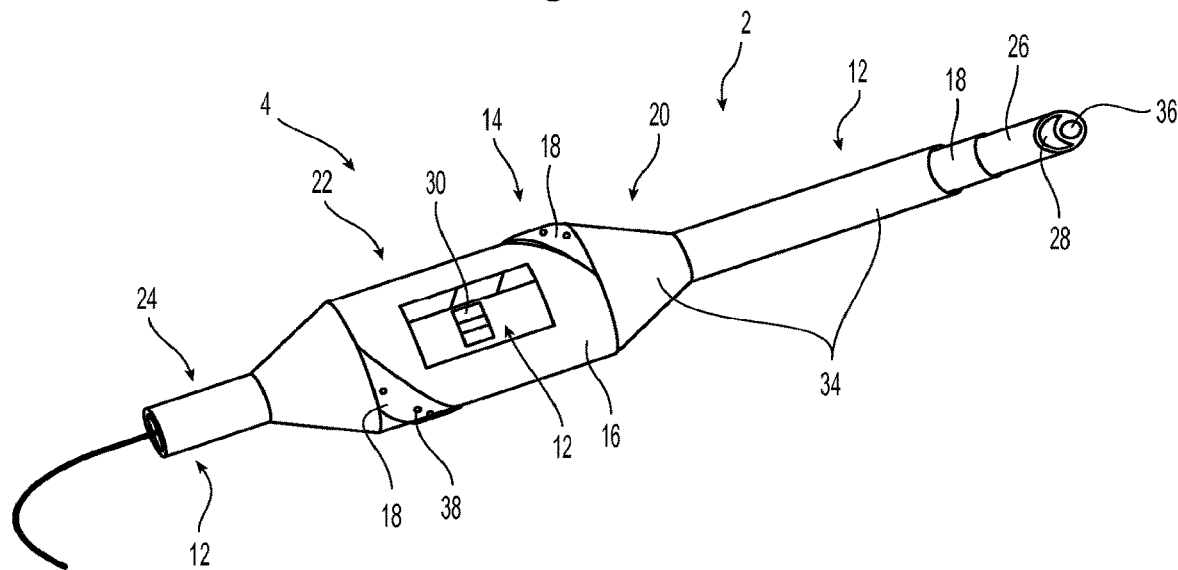

FIG. 1B illustrates a perspective view of the portion of the device shown in FIG. 1A, with a rectangular section of inflatable element 16 removed to illustrate elongate portion 12 disposed inside inflatable element 16.

Figure 2:
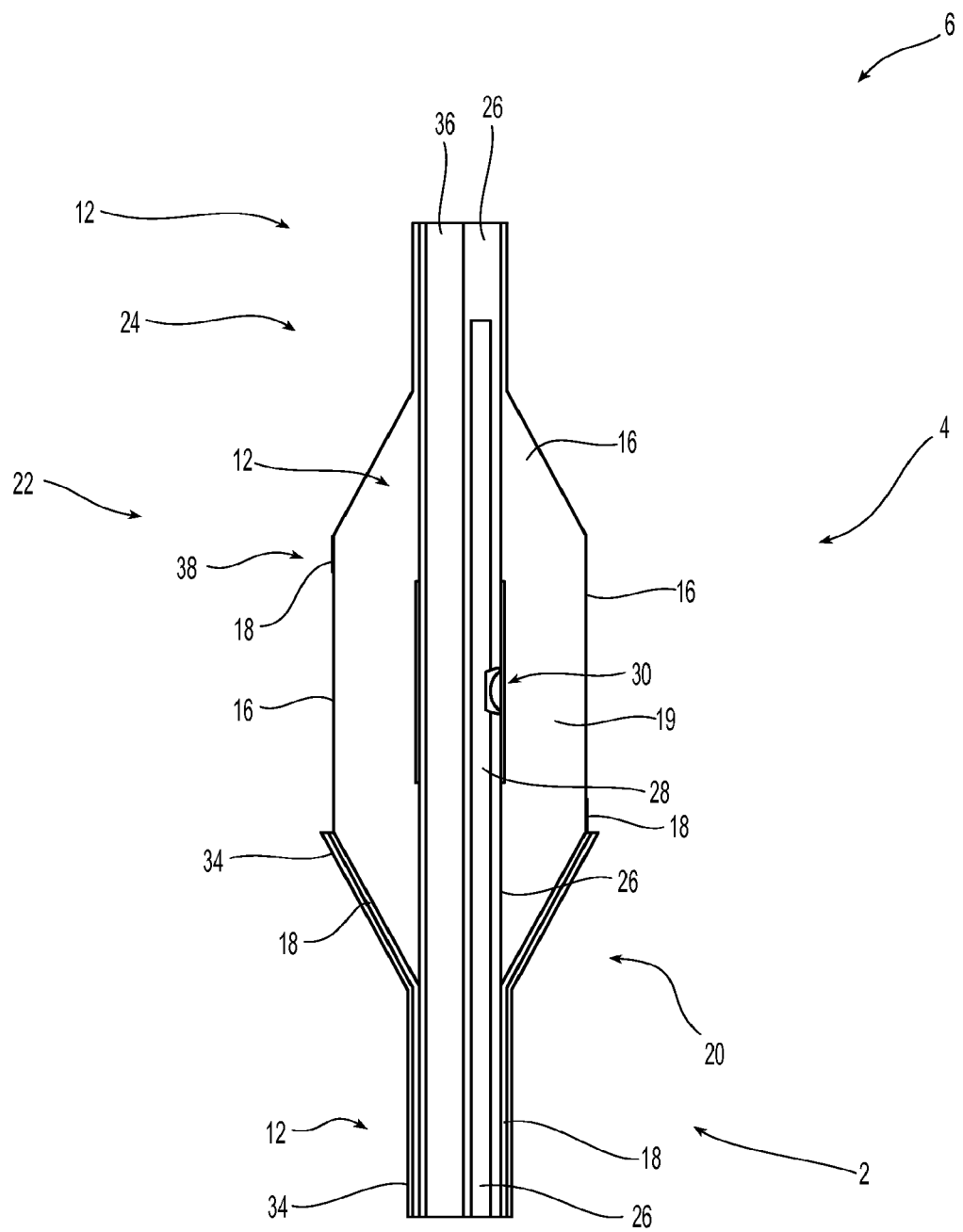

FIG. 2 shows a sectional view of the portion of the device shown in FIG. 1A. Expandable portion 14 includes a proximal transition section 20, intermediate section 22, and distal transition section 24. Proximal transition section 20 and distal transition section 24 are shown with conical configurations extending towards elongate portion 12 but are not limited to this configuration. Intermediate section 22 is substantially cylindrically-shaped when inflatable element 16 is in the expanded configuration shown in FIGS. 1A, 1B, and 2. The proximal end of inflatable element 16 and the distal end of inflatable element 16 are secured to catheter 26, which is part of elongate portion 12.

Conductive material 18 is disposed on catheter 26 proximal to the expandable portion 14, and it is also disposed on the cylindrical section of inflatable element 16 in a helical pattern forming a helical electrode 19 as shown. In proximal region 2 and in proximal section 20 of the expandable portion, insulation material 34 is disposed on the layer of conductive material 18. In the cylindrical intermediate section 22 of expandable portion 14, insulation material 34 is not disposed on the helical electrode, allowing energy to be delivered to tissue through conductive material 18. In the proximal region 2 of the device, and in proximal section 20 of expandable portion 14, conductive material 18 is covered with a layer of insulation, and thus energy is not applied to tissue in those areas. The conductive material that is not covered by dielectric material on the distal portion of the system is considered an electrode. The conductive material and the electrode are in this embodiment the same material.

The conductive material 18 is disposed on substantially the entire catheter 26 in proximal region 2 of the device. "Substantially the entire," or "substantially all," or derivatives thereof as used herein include the entire surface of catheter 26, but also includes most of the surface of the catheter. For example, if a few inches of the proximal end of catheter 26 are not covered with conductive material, conductive material is still considered to be disposed on substantially all of the catheter. The conductive material 18 and insulation material 34 extend 360 degrees around the catheter shaft, as opposed to only covering discrete lateral sections of the catheter. Alternatively, in some embodiments the conductor covers only a portion of the lateral surface of the catheter shaft. The conductive material and insulation material may cover the entirety or only a portion of the proximal transition section of the expandable portion. The insulation will typically cover the entirety of the conductive material in this region. The conductive material and insulation material could, however, also be disposed on the distal section 24 of expandable portion 14.

In some embodiments the helical electrode makes about 0.5 revolutions to about 1.5 revolutions around the inflatable element. The number of revolutions is measured over the length of the helical electrode. The electrode may extend from the proximal transition section to the distal transition section (as shown in FIG. 2), but the electrode may extend over any section of the inflatable element. For example, the proximal end of the electrode may be disposed distal to the proximal transition section, and the distal end of the electrode may be proximal to the distal transition section.

One revolution traverses 360 degrees around the longitudinal axis of the expandable element. One revolution of the electrode, along an end-view of inflatable device, forms a circle, although depending on the cross sectional shape of the expandable element, the electrode can form any variety of shapes in an end-view. An electrode making 0.5 revolutions therefore traverses one half of 360 degrees, or 180 degrees. An electrode making 0.5 revolutions has distal and proximal ends that are on opposite sides of the balloon. In an end-view of the inflatable element with a circular cross section, an electrode making 0.5 revolutions has a semicircular, or C, shape.

The proximal end of the electrode can be disposed anywhere on the expandable element and the distal end of the electrode can be anywhere on the expandable element, as long as the proximal end is proximal to the distal end. In some embodiments, the proximal end of the electrode is at the boundary between the proximal transition section and the cylindrical intermediate section of the expandable element, and the distal end of the electrode is at the boundary between the distal transition section and the cylindrical intermediate section. In other embodiments the proximal end of the electrode is disposed distal to the boundary between the proximal intermediate section and the cylindrical intermediate section of the expandable element, and the distal end is proximal to the boundary between the distal transition section and the central intermediate section of the expandable element. In these other embodiments the electrode is considered to extend along a subset of the length of the central intermediate section of the expandable element. In the embodiment shown in FIG. 1B, the electrode makes about 1 revolution around the inflatable element. In some embodiments the electrode makes about 0.5 revolutions around the inflatable element. In some embodiments the electrode makes about 0.75 revolutions around the inflatable element. In some embodiments the electrode makes about 1 revolution around the inflatable element. In some embodiments the electrode makes about 1.25 revolutions around the inflatable element. In some embodiments the electrode makes about 1.5 revolutions around the inflatable element.

The device is adapted to be coupled to an RF generator, which supplies RF current through the conductive material 18 on catheter 26 and inflatable element 16. In this manner RF current can be delivered to the desired tissue. Energy is thus applied to tissue in the configuration of the conductive material on the intermediate section 22 of the expandable portion 14, which in this embodiment is a helical, or spiral, configuration.

Figure 3A:
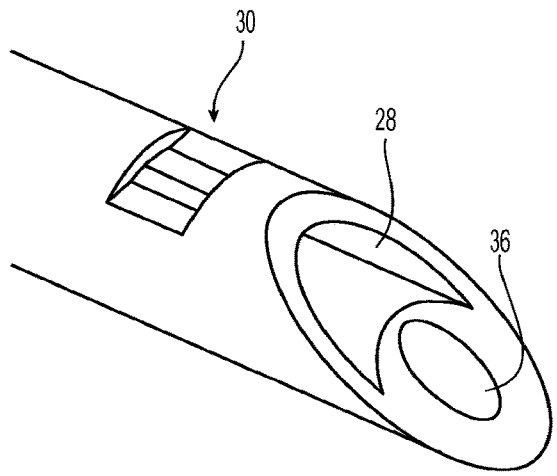
FIGS. 3A and 3B show a portion of an elongate device according to an embodiment of the present disclosure.
Figure 3B:
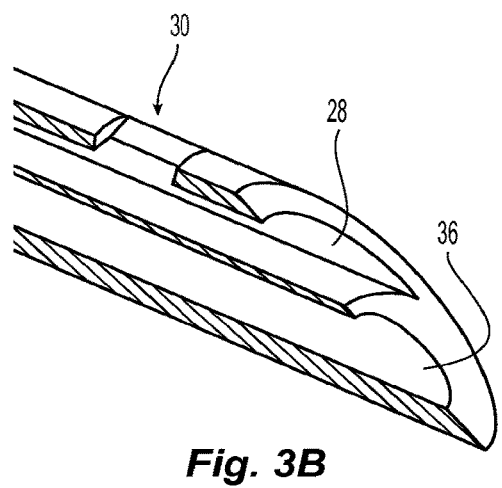

Within the expandable portion, catheter 26 is not covered with conductive material or insulation material. Catheter 26 includes guide element lumen 36 and inflation lumen 28, also referred to herein as irrigation lumen, extending therethrough. Guide element lumen 36 extends from the proximal end of the device (not shown) to the distal end. Irrigation lumen 28 extends from the proximal end of catheter 26 (not shown) to a location within inflatable element 16. Irrigation port 30 is located inside inflatable element 16 and is in between proximal and distal ends of irrigation lumen 28. Irrigation lumen 28 and irrigation port 30 provide for fluid communication between the irrigation lumen and the interior of inflatable element 16. FIGS. 3A and 3B illustrate additional views of guide element lumen 36, irrigation lumen 28, and irrigation port 30. In some embodiments catheter 26 ranges in size from 2 to 8 French, and in some embodiments is 4 Fr. In some embodiments the guide wire lumen is between 1 and 4 Fr and in some embodiments is 2.5 Fr.

Expandable portion 14 includes one or more irrigation apertures 38 to allow irrigation fluid to pass from inside inflatable element 16 to outside inflatable element 16. The irrigation apertures can be formed only in the electrode section of expandable portion 14 (see, for example, FIG. 1A), only in the non-electrode section of inflatable portion 14, or in both the electrode section and in the non-electrode section. The irrigation fluid is adapted to cool the conductive material 18 and/or tissue. The apertures allow for fluid to flow out of the balloon, allowing either a continuous or non-continuous supply of fluid from a fluid reservoir, through the lumen, and into the balloon. The irrigation fluid is in some embodiments cooled prior to delivery.

Figure 4:
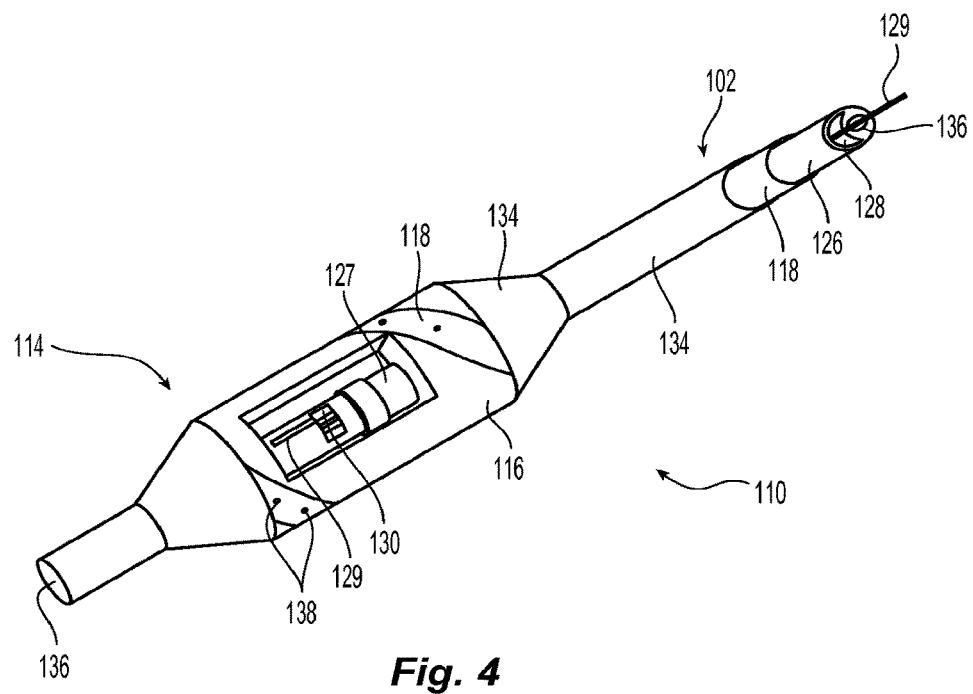
FIG. 4 shows a portion of an energy delivery device comprising a temperature sensor according to an embodiment of the present disclosure.

FIG. 4 illustrates a portion of an embodiment of a RF delivery device. Delivery device 110 is similar to the RF delivery device shown in FIGS. 1-3. Device 110 includes catheter shaft 126 covered with conductive material 118, upon which insulation material 134 is disposed. Insulation material 134 is also disposed on the proximal transition section of the expandable portion 114, similar to the embodiment shown in FIGS. 1-3. The inflatable element also has conductive material 118 disposed on the inflatable element in the form of a helical electrode. Catheter 126 has guiding element lumen 136 and irrigation lumen 128 therein. Device 110 also includes at least one marker 127 disposed on catheter 126 such that the marker is within expandable portion 114 (shown as a balloon). Device 110 also includes irrigation port 130 in fluid communication with irrigation lumen 134. Device 110 also includes temperature sensor 129, such as a thermocouple, a resistance temperature detector, or a thermistor, that is electrically coupled from the proximal end of the device (not shown) through irrigation lumen 128, out of irrigation port 130, and is secured at its distal region to catheter 126. The temperature sensor could alternatively be disposed on the inner or outer surface of inflatable element 116. In some embodiments marker 127 is a radio opaque marker comprised of Pt, PtIr, or other suitable radio opaque material. In some embodiments the marker may also comprise features viewable under fluoroscopy that allow for the visualization of the rotational orientation of the marker, and therefore the expandable section. This allows the physician to note the location of and/or realign the expandable element and helical electrode as necessary within the renal artery.

Figure 5:
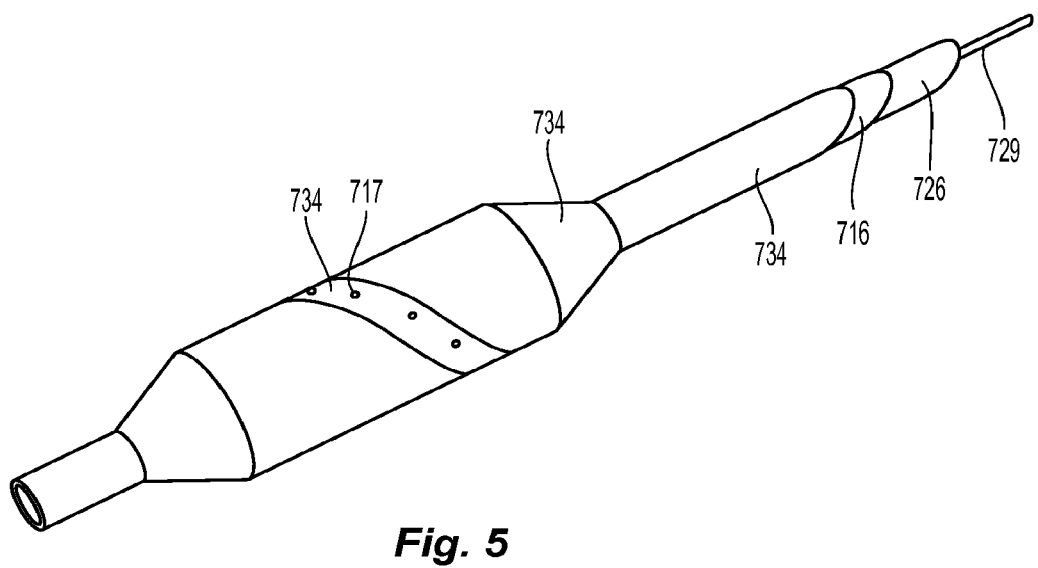
FIG. 5 illustrates a portion of an energy delivery device wherein portions of a helical electrode are covered with an insulation material according to an embodiment of the present disclosure.

The irrigation fluid is adapted to cool the electrode on the inflatable element. The irrigation fluid cools the RF electrode as it flows within the inflatable element and after it passes through the apertures as it flows across the outer surface of the inflatable element. Temperature sensor 129 is adapted to sense the temperature of the fluid within inflatable element 116. The signal from the temperature sensor may be used in a feedback control mechanism to control the flow of fluid from a fluid reservoir (now shown) into the inflatable element. Alternatively, the irrigation fluid may be delivered at a substantially constant rate and the signal from the temperature sensor used as signal to automatically shut off the RF generator if the sensed fluid temperature is above a threshold limit, thereby terminating that portion of the procedure. Such a condition is considered a fault and after identification and resolution of a fault, a procedure may be restarted. FIG. 5 illustrates a delivery device in which portions of the helical conductor have been covered by insulation material 734, forming a plurality of discrete circularly-shaped windows surrounding apertures 717 on electrical conductor 718. In this fashion a single conductor can be used to create a number of discrete burn zones following a helical path along and around a vessel wall.

In some embodiments, an anesthetic (such as lidocaine) may be added to the irrigation fluid, in order to reduce patient discomfort. In some such embodiments, it might be desirable to deliver the irrigation fluid and anesthetic at a higher pressure in order to achieve better tissue passage. The anesthetic may be introduced as a bolus in the initial part of the balloon inflation and electrode irrigation procedure. Alternatively, the balloon may be inflated with an anesthetic solution prior to RF energy delivery, then deflated to remove the anesthetic solution followed by reinflation with a saline solution to serve as the irrigation for the RF procedure. Delivery of the anesthetic solution may be preceded by inflation of the balloon (such as, e.g., with a contrast agent in the balloon or with saline in the balloon and contrast agent injected proximally to the balloon) to confirm positioning. Additional embodiments of energy delivery devices incorporating systems for delivery of anesthetic solution will be discussed hereinbelow.

Figure 6:
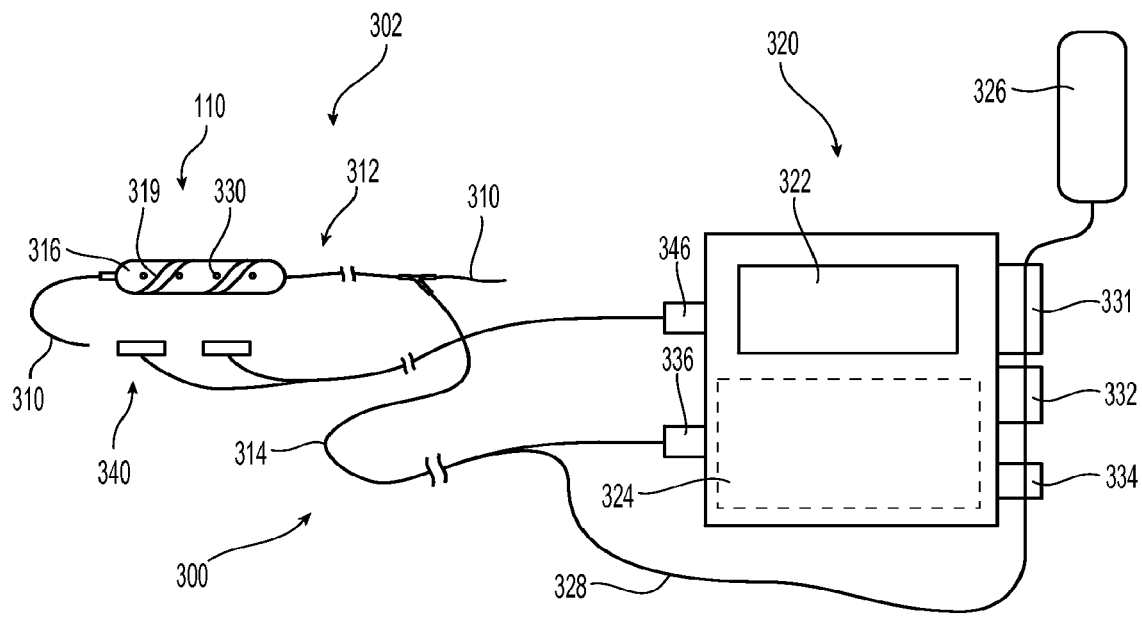
FIG. 6 illustrates an system for delivering energy to tissue according to an embodiment of the present disclosure.

One aspect of the disclosure is a system to delivery RF energy to treatment tissue. FIG. 6 illustrates a system 300 adapted to deliver RF energy to treatment tissue. System 300 includes RF energy delivery device 302, which can comprise any of the RF energy delivery devices described herein. Delivery device 302 is shown including inflatable element 316, helical energy delivery element 319, irrigation apertures 330, guidewire 310, and elongate member 312. System 300 also includes external housing 320, which includes display 322 and controller 324. Housing includes connector 336, which is adapted to connect to instrument interface cable 314. System 300 also includes fluid reservoir 326, which is in fluid communication with delivery device 302 via irrigation line 328. The system also includes fluid pump 331, optional pressure sensor 332, and optional bubble sensor 334. System 300 also includes a grounding plate or set of grounding plates 340 interfaced to controller 324 via connector 346.

Figure 14:
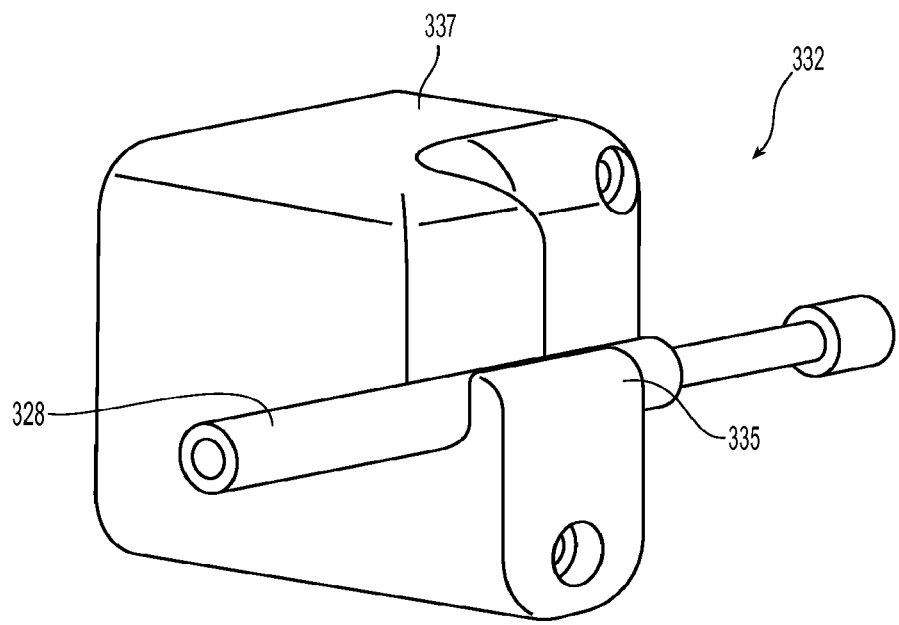
FIGS. 14 and 15 illustrate an embodiment of a pressure sensor according to an embodiment of the present disclosure.
Figure 15:
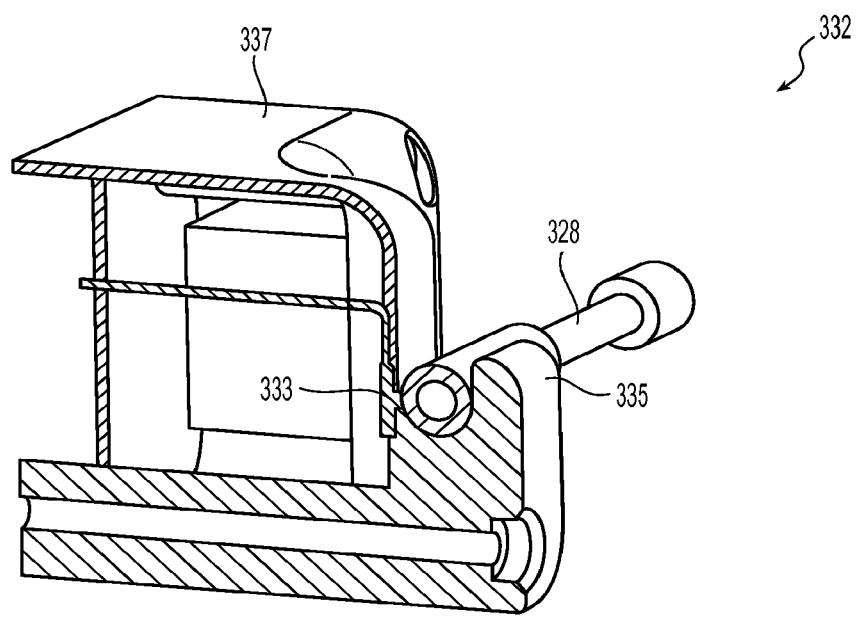

An embodiment of pressure sensor 332 from the system in FIG. 6 is shown in FIGS. 14 and 15. Pressure sensor 332 includes a housing, which comprises capture portion 335 and a force sensor 333. Capture portion 335 is configured to substantially surround irrigation tube 328. Additionally, capture portion 335 captures tubing 328 such that a portion of the wall of irrigation tube 328 is compressed against force sensor 333. The force experienced by the force sensor is then a function of the force associated by the compression of the irrigation tube and the pressure within the irrigation tube. In operation, a measurement is made under a no flow condition that describes the offset associated with the compression of the irrigation tube. This offset measurement is made prior to the initiation of a procedure and may be repeated at the beginning of each power cycle. This value is then used as an offset for subsequent measurements made under flow conditions. A force/pressure calibration per tubing type or per tube is then used to convert the force signal to a pressure value.

The disclosure includes methods of using any of the RF delivery devices and systems herein. In some embodiments the devices and/or systems are used to treat hypertension by disrupting the transmission within renal nerves adjacent one or both renal arteries.

The present methods control renal neuromodulation via thermal heating mechanisms. Many embodiments of such methods and systems may reduce renal sympathetic nerve activity. Thermally-induced neuromodulation may be achieved by heating structures associated with renal neural activity via an apparatus positioned proximate to target neural fibers. Thermally-induced neuromodulation can be achieved by applying thermal stress to neural structures through heating for influencing or altering these structures. Additionally or alternatively, the thermal neuromodulation can be due to, at least in part, alteration of vascular structures such as arteries, arterioles, capillaries, or veins that perfuse the target neural fibers or surrounding tissue.

Thermal heating mechanisms for neuromodulation include both thermal ablation and non-ablative thermal alteration or damage (e.g., via sustained heating or resistive heating). Thermal heating mechanisms may include raising the temperature of target neural fibers above a desired threshold to achieve non-ablative thermal alteration, or above a higher temperature to achieve ablative thermal alteration. For example, the target temperature can be above body temperature (e.g., approximately 37 degrees C.) but less than about 45 degrees C. for non-ablative thermal alteration, or the target temperature can be about 45 degrees C. or higher for the ablative thermal alteration.

The length of exposure to thermal stimuli may be specified to affect an extent or degree of efficacy of the thermal neuromodulation. For example, the duration of exposure can be as short as about 5, about 10, about 15, about 20, about 25, or about 30 seconds, or could be longer, such as about 1 minute, or even longer, such as about 2 minutes. In other embodiments, the exposure can be intermittent or continuous to achieve the desired result.

In some embodiments, thermally-induced renal neuromodulation may be achieved via generation and/or application of thermal energy to the target neural fibers, such as through application of a "thermal" energy field, including, electromagnetic energy, radiofrequency, ultrasound (including high-intensity focused ultrasound), microwave, light energy (including laser, infrared and near-infrared) etc., to the target neural fibers. For example, thermally-induced renal neuromodulation may be achieved via delivery of a pulsed or continuous thermal energy field to the target neural fibers. The energy field can be sufficient magnitude and/or duration to thermally induce the neuromodulation in the target fibers (e.g., to heat or thermally ablate or necrose the fibers). As described herein, additional and/or alternative methods and systems can also be used for thermally-induced renal neuromodulation.

The energy field thermally modulates the activity along neural fibers that contribute to renal function via heating. In several embodiments, the thermal modulation at least partially denervates the kidney innervated by the neural fibers via heating. This may be achieved, for example, via thermal ablation or non-ablative alteration of the target neural fibers.

In some uses in which RF energy is used to ablate the renal nerve, the RF delivery device is first positioned within one or more renal arteries and RF energy is delivered into renal nerves to disrupt the nerve transmission sufficiently to treat hypertension. The disruption pattern within the artery preferably extends substantially 360 degrees around the artery. Electrodes that treat tissue falling diametrically in a single plane normal or oblique to the longitudinal axis of the vessel have been shown to increase the risk of stenosing a vessel treated with RF energy. Spiral, or helical, patterns as described herein create patterns of treated tissue for which the projection along the longitudinal axis is circular and therefore have a high probability of treating any renal nerve passing along the periphery of the renal artery. The patterns, however, have minimal risk of creating a stenosis. Previous attempts have used a point electrode at a distal end or distal region of a device. In these attempts, the electrode is disposed in the renal artery followed by RF energy delivery. To disrupt renal nerve tissue in a non circumferential pattern using a point electrode, the device is first positioned within the renal artery adjacent arterial tissue. RF energy is then delivered to disrupt a region of renal nerve. The device must then be moved axially (distally or proximally) and rotated, followed by additional RF delivery. The movement and RF delivery is repeated in a pattern until the renal nerves have been sufficiently disrupted. The repeated movements are time consuming and increase the complexity of the overall process for the physician. During an emergency situation the physician may lose track of the position and sequence of previous burns thereby jeopardizing the likelihood of creating a pattern sufficient to treat the neural tissue or be forced to increase the number of burns thereby over-treating the patient.

Utilizing a single helical electrode as described herein provides procedural improvements over previous attempts. By using an electrode with the configuration of the desired treatment region, the device need not be moved to disrupt tissue in a desired treatment configuration. In particular the device need not be moved axially or rotated to treat an entire renal nerve treatment region. This reduces the overall time of the treatment. Additionally, this allows energy to be delivered to a desired treatment region in a variety of patients with much greater predictability. Additionally, if markers are used that allow for rotational alignment, the device may be moved and/or removed and then replaced and realigned, allowing the procedure to be restarted at a later time.

Figure 7:
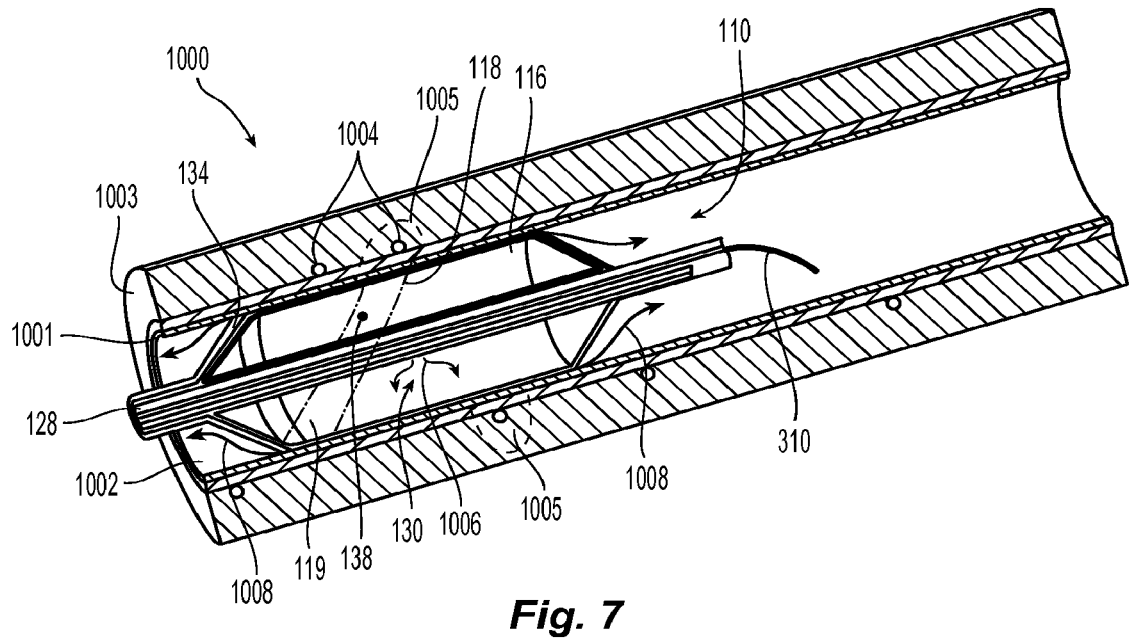
FIG. 7 illustrates a cross section of an energy delivery device with a helical electrode in use within a renal artery according to an embodiment of the present disclosure.

A method of using an RF delivery device to treat hypertension is shown in FIG. 7, and will be described using the device in FIG. 4 and the system shown in FIG. 6. The methods described herein can be carried out by other systems and by other RF delivery devices, such as the RF devices described herein.

The RF delivery device is positioned in a renal artery using a percutaneous access through a femoral artery. The expandable portion is delivered into the renal artery in a collapsed configuration (not shown). Once the expandable portion is in position, fluid from fluid reservoir 326 is pumped in an open loop control configuration, under constant flow, through irrigation line 328 and into inflatable element 116 by pump 330. Fluid flow into inflatable element 116 causes inflatable element 116 to expand. Device 110 in FIG. 7 is in a delivered, or expanded, configuration within renal artery 1000. The tunica intima 1001 is surrounded by the tunica media 1002, which is in turn surrounded by adventitial tissue 1003. Tissue renal nerves 1004 are shown within the adventitial, and some renal nerves not shown will be found within the tunica media.

The fluid continually passes through apertures 138 in the expandable portion as it is replaced with new fluid from fluid reservoir 326. Once fully expanded, the conductive material 118 on the inflatable element fully assumes the helical configuration, as shown in FIGS. 4 and 7. RF energy is then delivered to the helical electrode on the inflatable element. Control unit 324 controls the parameters of the RF alternating current being delivered through the conductive material on the catheter and the helical electrode on the inflatable element.

In general, the RF signal characteristics are chosen to apply energy to depths at which the renal nerves are disposed to effectively ablate the renal nerves. In general, the power is selected to ablate a majority of the renal nerves adjacent to where the device is positioned within the renal nerve. In some embodiments the tissue is ablated to a depth of between about 3 mm to about 7 mm from the tissue closest to the device in the renal artery.

The RF signal can have the following characteristics, but these are not intended to be limiting: the frequency is between about 400 KHz to about 500 KHz and is a sine wave; the power is between about 30 W to about 80 W, the voltage is between about 40v and about 80v; and the signal is an intermittent signal.

Tissue treated by the RF energy via the helical electrode comprised is shown as regions 1005, delineated by a dashed line. As illustrated, a region of treated tissue 1005 adjacent to the cut away section of conductor 118 includes nerve 1004. The device is shown being used in monopolar mode with a return electrode 340 positioned somewhere on the patient's skin.

Control unit 324 controls the operation of pump 330 and therefore controls the flow rate of the fluid from reservoir into the inflatable element. In some embodiments the pump is continuously pumping at constant flow rate such that the flow is continuous from the reservoir, as is illustrated in FIG. 7. In some embodiments the pump is operated in an open loop constant flow configuration where pump rate is not adjusted as a function of any control parameter other than an over-pressure condition sensed by pressure sensor 332, in which case RF power delivery is terminated, the pump is turned off, and an over-pressure condition reported to the operator. The pump is typically operated for a period of time which encompasses the delivery of the RF energy and turned off shortly after the conclusion of the procedure or if the pressure sensor senses an undesirable condition, discussed herein.

The irrigation fluid is delivered from the pump through irrigation line 328 to irrigation lumen 128 to irrigation port 130 into the inflatable element 116, and then out of the inflatable element through irrigation apertures 138. The pressure measured at the pressure sensor is driven by flow rate and the series sum of the fluid resistance of all of the elements in the fluid path. The choice of fluid flow rate is driven by the required cooling rate and limited by the amount of irrigant fluid that can be tolerated by the patient which is delivered during the sum of treatments cycles. The system is designed such that at the desired fluid flow there is a defined operating pressure within the inflatable element. An optimal inflatable element inflation pressure is a pressure that is sufficient to completely inflate the inflatable element such that the RF electrode engages the treatment tissue. The operating pressure within the inflatable element will be driven by the fluid flow, the number of apertures, and their cross sections. The distribution, number, and cross section of the irrigation apertures will be driven by the flow rate, the configuration of the electrode, the intended operating pressure, and the maximum desired exit velocity for the irrigation fluid. If the number of apertures is too small and the distribution too sparse some areas of the surface will not receive appropriate irrigation and thereby be subject to overheating and possible charring of tissue. For a set of circular apertures and a given flow rate, the mean exit velocity for the irrigation fluid will drop as the number of apertures is increased while decreasing the cross sectional area of each aperture such that the fluid resistance of the sum of apertures is appropriate to maintain the desired inflation pressure. Minimizing the irrigation fluid exit velocity minimizes or precludes the possibility that lesions will be eroded through the treatment tissue.

A set of operating conditions and design parameters is now provided, and is not meant to be limiting. An inflation pressure between about 0.5 atm and less than about 4 atm used with a noncompliant inflatable element of approximately 0.75 mil (~19 um) thick ensures tissue engagement in a renal artery. In some particular embodiments the inflation pressure is about 2 atm+/−0.5 atm. The irrigation fluid delivery rate is between about 1 mL/min and about 20 ml/min. In some particular embodiments the delivery rate is about 10 mL/min+/−2 mL/min. The expandable portion includes eight irrigation apertures about 2.6 mil (0.0026 inches) in diameter distributed on either side of the helical electrode and equally spaced along the edge of the electrode. In such a configuration the mean exit velocity is about 6 m/sec. In some embodiments the maximum mean fluid exit velocity is between about 1 m/sec and about 20 m/sec.

The above operating parameters are not intended to be limiting. For example, the inflation pressure can be between about 0.5 atm (or less) and about 10 atm, the flow rate can be between about 1 mL/min to about 50 mL/min, and any suitable number of apertures with any suitable size can be incorporated into the device. Apertures may be of the same size or of different sizes and may also be uniformly or non-uniformly distributed through and/or about the electrode. The apertures are sized such that the total resistance of the set of apertures is appropriate to maintain the pressures defined herein internal to the inflatable element at the desired flows described herein. Alternatively, the total resistance is such that the desired flows described herein are maintained at the desired pressures described herein. The total resistance for the parallel combination of apertures is calculated as the inverse of the sum of the inverses of the individual aperture resistances.

The system shown also includes pressure sensor 332, which is adapted to determine if the pressure rises above or below threshold limits. If the fluid pressure rises above an established limit, the controller shuts off the RF energy, and fluid pump 330 is automatically shut off. The pressure can elevate if one or more of the apertures become blocked, preventing fluid from passing out of the balloon, which can prevent the electrode from being cooled sufficiently. Controller 324 therefore runs fluid pump 330 in a binary manner, either open-flow or off.

The system as shown also includes a temperature sensor 129 secured to the catheter within the inflatable element. If the sensed temperature of the fluid is above a threshold limit, the fluid will not properly cool the electrode. If the sensed fluid temperature is above a threshold limit, control unit 324 is adapted to cease RF current delivery. The fluid temperature in the balloon can rise if one or more apertures are blocked, preventing the electrode from being properly cooled and also increasing the risk of charring. The fluid pressure generally will rise above a threshold limit if this occurs as well. In some embodiments the system has only one of the temperature sensor and pressure sensor.

The system may also include bubble sensor 334, which is adapted to sense bubble s in the fluid line and communicates with control unit 324 to shut off pump 330 if bubbles of sufficient volume are detected.

The system can also include a flow sensor to determine if the flow rate has gone below or above threshold limits. RF energy delivery is automatically stopped and the pump is automatically shut down if the flow rate goes above or below the threshold limits.

In an alternate embodiment to that of FIG. 6 the constant flow control of the system may be replaced by constant pressure control. In such a system the reservoir 326 may be maintained at a pressure within the prescribed pressure range using, for example without limitation, an IV bag pressure cuff or other suitable means, and the pump replaced by a flow sensor or flow controller. In such a system pressure is maintained at a substantially constant level within the prescribed range and flow rate monitored. When flow rate falls outside of the proscribed range the RF power delivery is terminated.

In general, using a greater number of smaller holes provides substantially the same resistance as a fewer number of larger holes, but mean fluid exit velocity is diminished.

Figure 8:
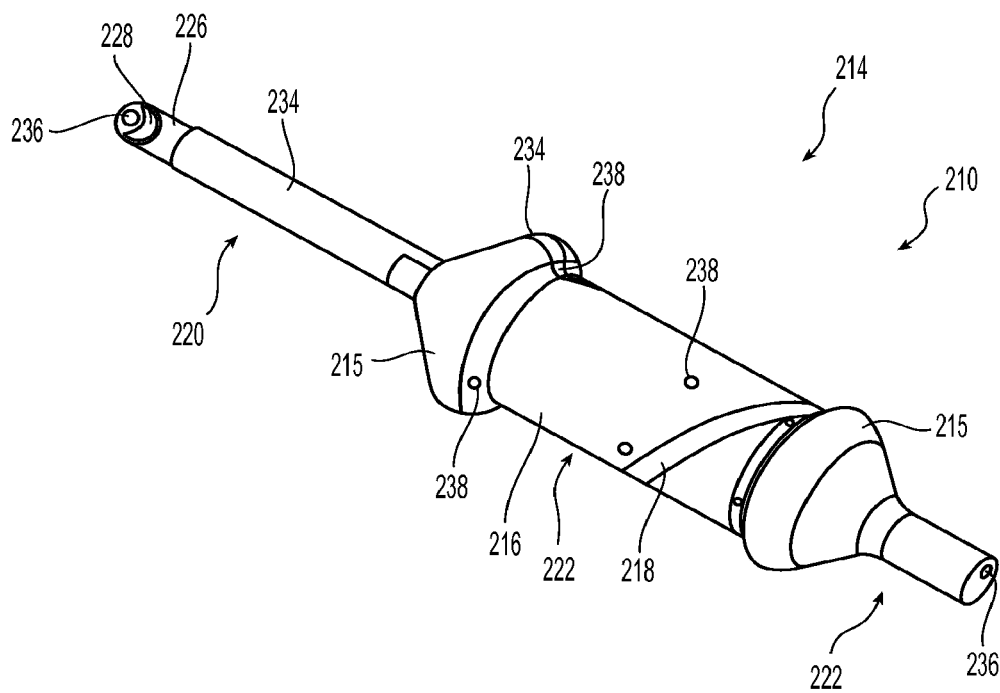
FIGS. 8 and 9 illustrate a portion of an energy delivery device wherein energy is delivered to renal nerves through conductive fluid to the tissue according to an embodiment of the present disclosure.

FIG. 8 illustrates a portion of an embodiment of an RF delivery device wherein the expandable portion has a general dumbbell configuration, and energy is delivered through the conductive fluid to the tissue. RF delivery device 210 includes expandable portion 222 that comprises inflatable element 216 on which is disposed conduction material 218 with a helical configuration. The catheter has guiding element lumen 236 and irrigation lumen 228. A conductive layer and an insulation layer are disposed on the catheter as in the embodiment in FIGS. 1-5. The proximal and distal portions of inflatable element 216 have diameters that are greater than the intermediate section, such that the expandable portion has a general dumbbell shape. When inflated, larger diameter proximal and distal ends of the expandable portion 214 contact the vessel wall, while space is left between the cylindrical section 222 of the expandable element and the vessel wall as illustrated in FIG. 8. The irrigation fluid flowing through irrigation apertures 238 fills the space between the cylindrical section 222 and tissue, and current from the helical electrode is carried through the conductive irrigation fluid and into the adjacent tissue. In this configuration the helical electrode does not contact tissue directly, therefore the uniformity of heating is improved and the risk of charring or overheating the tissue is reduced.

Device 210 is also adapted to query the nervous tissues adjacent to the device, but need not include this functionality. Device 210 includes nerve conduction electrodes 215 located on the outer surface of the dumbbell shaped proximal and distal ends of the expandable portion 214. In use, an electrical signal, typically a low current pulse or group of pulses is transmitted to one of the conduction electrodes. This triggers a response in adjacent renal nerves, which then travels along the nerves and at some time "t" later is sensed by the opposite electrode when the signal is traveling in the appropriate direction. By alternating which electrode is used as the exciter and which the sensor, both changes in efferent and afferent nerve conduction in the renal nerves may be monitored as a function of RF treatments induced by the RF electrode. The conduction electrodes are wired to the sensing circuits in the controller via wires traveling within the catheter shaft, as in the irrigation lumen, or additional lumens (not shown), or multiple conductors may be applied to the outer surface of the shaft (not shown).

Figure 9:
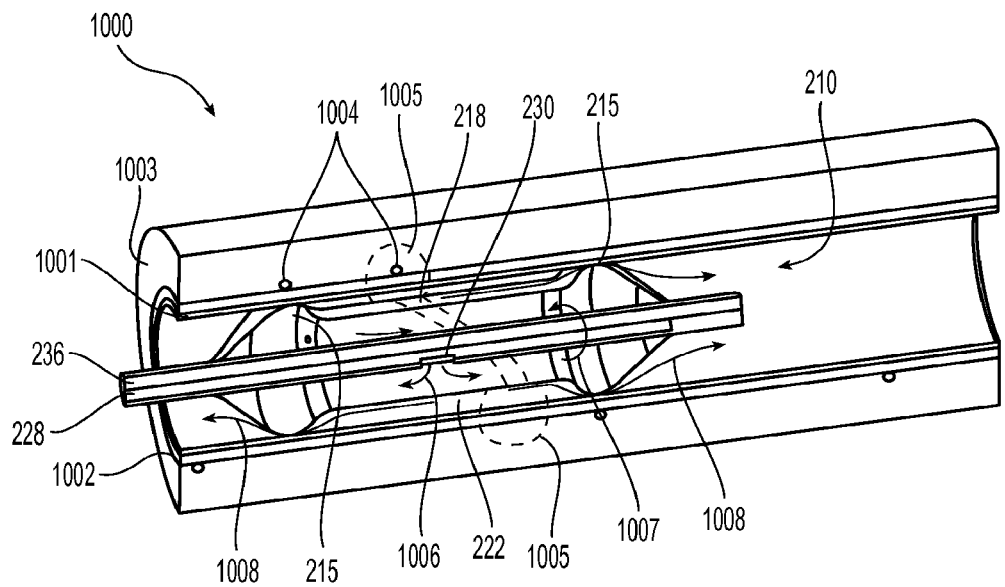

FIG. 9 illustrates the delivery device 210 in a delivered, or expanded, configuration within a renal artery. Areas 1005 indicate tissue treated by the application of RF energy delivered via the helical electrode. An area 1005 adjacent to conductor 218 surrounds a renal nerve 1004. Irrigation fluid movement is shown by the arrows. The fluid enters the inflatable element 216 at irrigation port 230 as shown by arrows 1006. The fluid then flows out of inflatable element 216 at irrigation apertures 238, shown by arrows 1007. The fluid then flows past conduction electrodes 215 into the blood stream, shown by arrows 1008.

In use, the dumbbell configuration creates a small space between the helical electrode and the arterial wall. The irrigation fluid, such as saline, can be used to act as a conductor and transfer energy from the electrode to the tissue. In such a system, the impedance variations, at the interface between the tissue and the electrode, associated with surface irregularities and variations in contact between the electrode and tissue will be minimized. In this manner the fluid can act both to cool the electrode and to transfer energy to tissue. The thin layer of fluid between the electrode and tissue can also prevent sticking and add lubrication.

Unless specifically stated to the contrary, the embodiment of FIG. 7 includes features associated with the embodiment from FIG. 4.

The configuration of RF delivery device 210 is less dependent on considerations listed above with respect to the embodiment in FIG. 4 as the irrigation fluid does not directly impinge on the treatment tissue and is allowed circulate in the space between the vessel wall and the cylindrical central section 222. Such a configuration additionally requires less irrigation fluid to prevent charring as the electrode 129 does not contact the tissue directly.

In use, the embodiment from FIG. 5 is used to create a discontinuous helical burn pattern formed of a plurality of discrete burn areas in the tissue. The helical burn pattern is formed during a single treatment session and does not require the device be moved to create the plurality of discrete burn areas.

Figure 10:
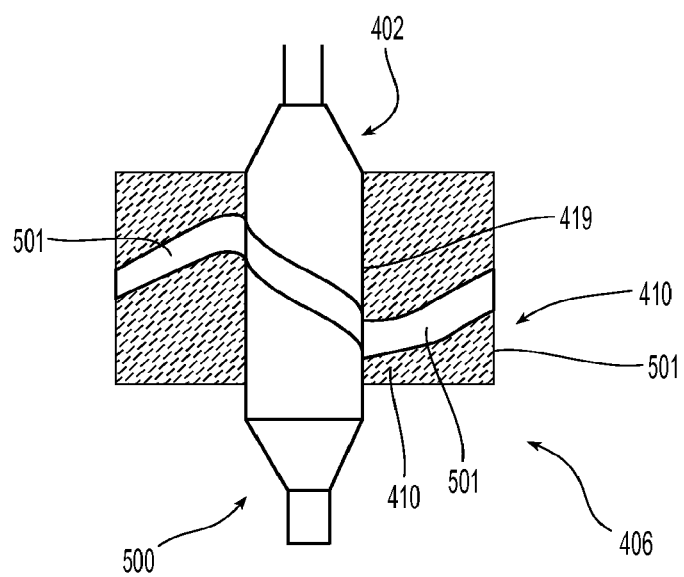
FIG. 10 is a photograph showing tissue ablation in a general helical pattern caused by an energy delivery device with a helical electrode according to an embodiment of the present disclosure.

FIG. 10 is a photograph of an RF delivery device 410 on top of a piece of heart tissue 500 which has been ablated with RF energy delivered by a device similar to that in FIG. 4 and a system similar to that of FIG. 6. The heart tissue was originally cut as a cylinder into the core of which the distal end 406 of the RF delivery device 410 was deployed. RF energy comprising a signal of 400K Hz at 40 volts and 40 watts was then delivered to the tissue. The cylinder of tissue was then cut along its length so that the inner surface of the tissue cylinder could be visualized. Helical burn zone 501 was created by helical electrode 419. The burn zone has the same configuration as the helical electrode.

Figure 11A:
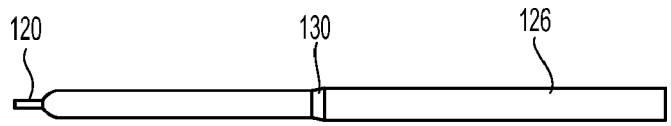
FIGS. 11A-11H illustrate a method of manufacturing an energy delivery device with a helical electrode on an expandable element according to an embodiment of the present disclosure.
Figure 11B:
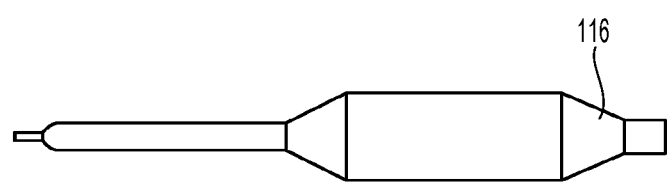

One aspect of the disclosure is a method of manufacturing RF delivery devices. FIGS. 11A-11H illustrate a method of manufacturing a portion of the RF delivery device 110 from FIG. 4. In FIG. 11A, catheter 126 is provided and can be any suitable catheter or other elongate device, such as a sheath. For example, catheter 126 can be an extruded material, and optionally can have a stiffening element therein such as a braided material. In this embodiment catheter 126 is extruded with a guide element lumen and an irrigation lumen formed therein (not shown), and the irrigation port is formed therein (not shown). The irrigation lumen is closed off at the distal end of the catheter to prevent fluid from escaping the distal end of catheter, but the irrigation lumen can stop at the irrigation port rather than continuing further towards the distal end.

Figure 11C:
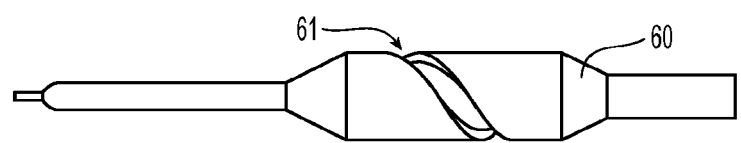
Figure 11D:
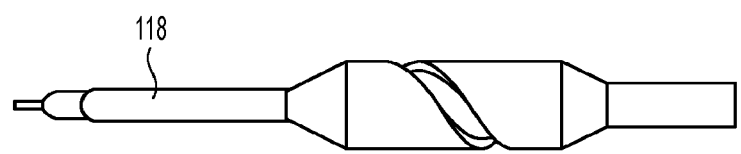
Figure 11E:
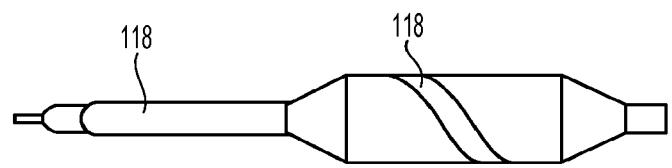
Figure 11F:
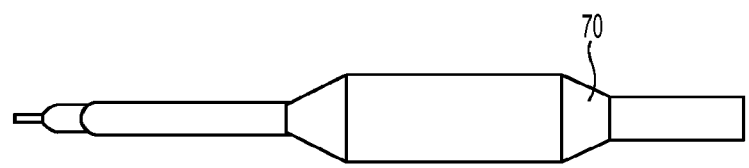
Figure 11G:
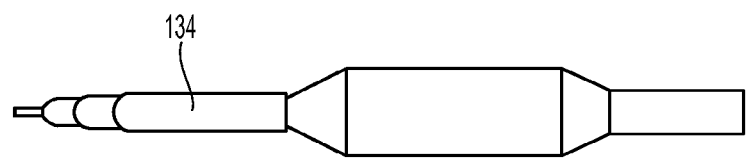
Figure 11H:
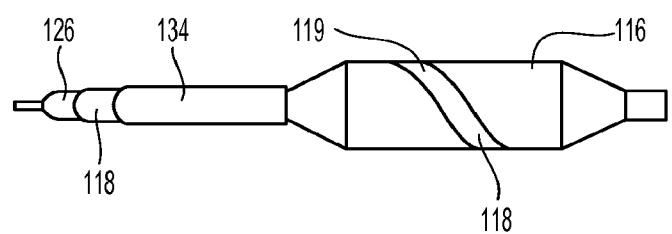

Inflatable element 116, which can be an inflatable balloon, is then secured to the exterior of catheter 126 using any suitable technique such that irrigation port 130 is disposed within inflatable element 116. Next, mask 60 is applied or slid over inflatable element 116. The mask is configured such that it covers areas where the conductive material is not to be deposited and is open where conductive material is to be applied. In FIG. 11C, mask 60 is configured with open area 61 to allow for the deposition of a conductive element 118 in a helical configuration. Inflatable element 116 is then inflated with a suitable inflation fluid (e.g., liquid or gas) delivered through the irrigation lumen and out port 130 to expand, or inflate, inflatable element 116, as shown in FIG. 11C. Additionally, mask 60 is typically configured to mask the distal transition section of the expandable portion and the catheter distal to the expandable portion. After mask 60 is applied, conductive material 118 is then deposited, in a single deposition step, onto substantially all of catheter 126, portions of inflatable element 116, and mask 60. This forms a conductive material layer on substantially all of catheter 26, proximal portion of inflatable element 116, and in the helical pattern on inflatable element 116. After the conduction material 118 is deposited in the single step and allowed to dry sufficiently and or cure, inflatable element 116 is deflated and the mask 60 is removed. As shown in FIG. 11F, a second mask 70 is then applied over those areas of conductive material 118 which are intended to deliver energy directly to the tissue in the energy delivery pattern, which is the helical pattern. The inflatable element 216 is then re-inflated and insulation material 34 is applied to substantially the entire device in a single depositing step as shown in FIG. 11G. This forms an insulation layer on substantially the entire conductive material already deposited on catheter 126, the proximal portion of the inflatable element, and the intermediate portion of the inflatable element where mask 70 is not disposed. Next, after appropriate drying and or curing the inflatable element is deflated and the mask 70 removed as shown in FIG. 11H. After mask 70 is removed, shaft 126, and proximal transition section of inflatable element is encapsulated by conductor 118 which are in turn encapsulated by dielectric 134, while helical conductive electrode 118 on the inflatable element is not covered with dielectric. The irrigation apertures are then formed, such as by laser drilling.

In some embodiments of manufacturing the device, the layers of conductive material and insulation material are between about 0.0001 and about 0.001 inches thick. In some embodiments the conductive layer is about 0.0003 inches thick. In some embodiments the insulation layer is about 0.0005 inches thick.

Alternate methods for deposition of the conductor and/or the dielectric layers which that can be used and do not require masking include ink jet and or pad printing techniques.

These methods of manufacturing form a unitary conductor. A "unitary conductor" as described herein is a single conductive material comprising both a conduction element and an electrode element wherein the conductive element communicates energy between the controller and the electrode element.

The conductive and insulation materials can each be deposited on substantially all of elongate portion 112 (excluding the portion within expandable portion 114) and expandable portion 114 in a single step, reducing the time necessary to form the conductive and insulation layers, respectively. This can also simplify the manufacturing process. To deposit the conductive and insulation material, the device can be secured to a mandrel and spun while the material is deposited, or the device can be secured in place while the device used to deposit the material is moved relative to the device, or a combination of the two steps. "Single step" as used herein includes a step that applies the material without stopping the deposition of material. For example, the conductive material can be deposited on substantially all of the catheter proximal to the inflatable element and to the inflatable element in a single step. "Single step" as used herein also includes applying a second or more coats to the elongate portion and the expandable portion after initially ceasing the deposition of material. For example, a process that applies a first coat of conductive material to substantially all of the catheter proximal to the inflatable element and to the inflatable element, followed by a ceasing of the deposition, but followed by application of a second coat to substantially the entire portion of the catheter proximal to the inflatable element and to the inflatable element, would be considered a "single step" as used herein. Some previous attempts to form a conductive material on an elongate device formed one or more discrete conductive elements on the elongate device, thus complicating the deposition process. These and other attempts failed to appreciate being able to form a single layer of conductive material on substantially all of the catheter or other elongate device. These attempts failed to appreciate being able to form single layer of conductive material on the catheter and an electrode element on an expandable element in a single step.

By disposing the conductive material on the external surfaces of the catheter and inflatable element in a single step, the creation of electrical junctions is avoided. For example, a junction need not be formed between the conductive material on the catheter and the conductive material on the inflatable element. As used herein, electrical junction refers to a connection created between two conductive materials, either the same or different materials, that allows an electrical signal to be conducted from one material to the other.

The inflatable element is, in some embodiments, an inflatable balloon that is adapted to be inflated upon the delivery of a fluid through the irrigation lumen and out of the irrigation port. In the embodiment in FIGS. 1-11, the inflatable element is a balloon made of non-elastic, or non-compliant, material, but it can be a compliant, or elastic, material as well. Materials for a non-compliant balloon include, without limitation, polyethylene, polyethylene terephthalate, polypropylene, cross-linked polyethylene, polyurethane, and polyimide. Materials for a compliant balloon include, without limitation, nylon, silicon, latex, and polyurethane.

In some embodiments of the embodiment in FIG. 4, the length of the cylindrical intermediate portion of the inflatable element is between about 1 cm and about 4 cm. In some embodiments the inflatable element has a diameter between about 4 mm and about 10 min. In some particular embodiments the length of the intermediate portion of the inflatable element is about 20 mm and the diameter is about 5 mm to about 7 mm.

The conductive material can be deposited onto the catheter and/or expandable portion. Methods of depositing include, without limitation, pad printing, screen printing, spraying, ink jet, vapor deposition, ion beam assisted deposition, electroplating, electroless plating, or other printed circuit manufacturing processes.

In some embodiments the conductive material deposited is an elastomeric ink and the dielectric material is an elastomeric ink. They can be sprayed on the respective components. In some embodiments the elastomeric ink is diluted with an appropriate diluent to an appropriate viscosity then sprayed in a number of coats while the delivery device is rotated beneath a linearly translating spray head.

Conductive materials that can be deposited on the device to form one or more conductive layers of the device include conductive inks (e.g., electrically conductive silver ink, electrically conductive carbon ink, an electrical conductive gold ink), conductive powders, conductive pastes, conductive epoxies, conductive adhesives, conductive polymers or polymeric materials such as elastomers, or other conductive materials.

In some embodiments the conductive material comprises an elastomeric matrix filled with conductive particles. Elastomeric components include silicones and polyurethanes. Conductive materials are conductive metals such as gold or silver. Conductive inks that can be used are conductive ink CI-1065 and CI-1036 manufactured by ECM of Delaware Ohio. This ink is an extremely abrasion resistant, flexible, and highly conductive elastomeric ink. The ink has the following properties: 65% solids in the form of silver flakes; 0.015 ohms/square (1 mil (0.001 inches) thick); and a 10 minute cure time at 248 F.

The electrodes described herein can also be used as a temperature sensor. Ablative electrodes are routinely used in wide variety of surgical procedures. Many of these procedures are performed percutaneously, and a subset are performed endovascularly. In many of these procedures it is customary to incorporate provisions to monitor the temperature of the ablative electrodes. This temperature information is then used in some fashion as an input in a control scheme to limit the maximum temperature the electrode is allowed to attain. In this fashion a number of mechanisms, that may be deleterious to the desired outcome, may be controlled and or limited. Some of these effects, which in some circumstances are considered deleterious are, tissue charring, creation of steam, and the resultant uncontrolled, rapid, or large changes in interface impedance.

The temperature monitoring is typically carried out by incorporating and mounting some form of a temperature sensor such as a thermocouple, an rdt, or a thermistor in proximity to, or on, the electrode.

The electrodes are typically comprised of metals or metal alloys which are either deposited as metals directly through various metal deposition procedures such as, but not limited to physical or chemical metal vapor deposition, or applied as a component in a matrix such as but not limited to organic polymers in the form of an ink. Such inks are deposited in many ways, a few of which are, screening, spraying, ink jetting.

Metals, metal alloys, and other metal compound have resistance characteristics which are dependent on temperature, typically called the temperature coefficient of resistance or "tempco." The magnitude and characteristics of these effects varies and is often used in devices such as a resistance temperature detector "RTD", such as a platinum rtd's, or in positive temperature coefficient "PTC" or negative temperature coefficient "NTC" thermistors.

The systems herein can therefore alternatively monitor temperature by using the inherent tempco of the electrode itself as a way of monitoring its temperature and or controlling its impedance and thereby self-limiting its power output and thereby its temperature.

Figure 12:
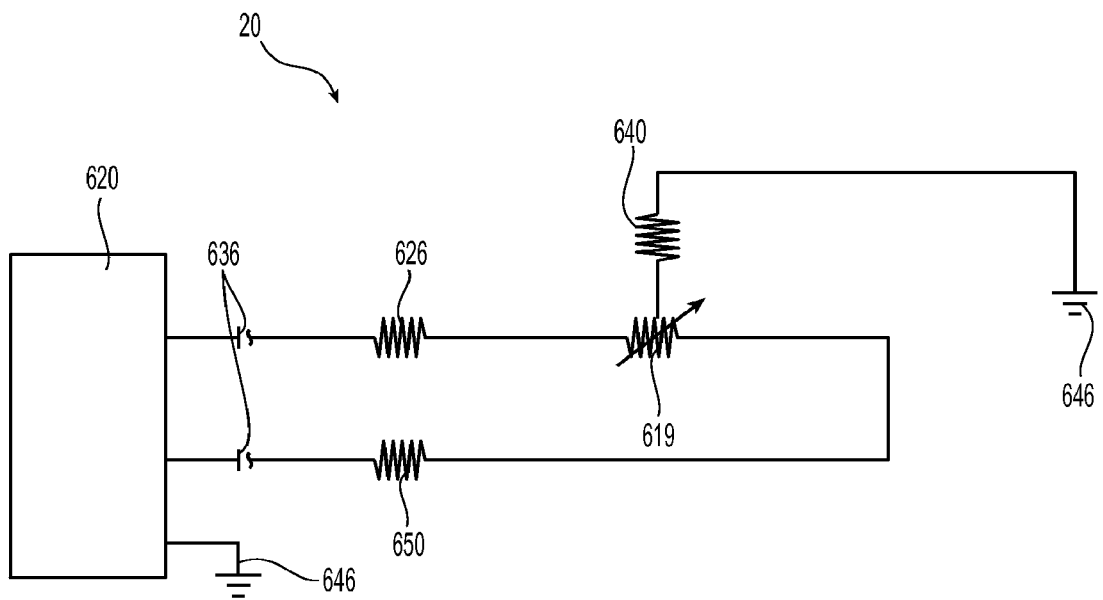
FIG. 12 represents an embodiment of a system similar to that of FIG. 6 represented by the resistances of the various elements according to an embodiment of the present disclosure.

FIG. 12 represents an embodiment of a system similar to that of FIG. 6 represented by the resistances of the various elements. The delivery RF lead which runs down catheter is represented as resistance 626 and the electrode is represented by resistance 619. In this embodiment there is an additional conductive element running along the catheter shaft which is a return line represented by resistance 650. In use the leads whose resistances are represented by 626 and 650 may be sourced in parallel when RF is delivered to electrode 619 and addressed separately when used to characterize the resistance and hence temperature of the electrode 619. Alternatively one of them may be used solely for the purpose of monitoring temperature and therefore left open circuited when RF is being delivered. The design of the delivery system and electrode will be such that the impedance 640 of the patient will be orders of magnitude greater then the impedances for the delivery leads 626, 650, and the electrode 619. In one embodiment impedance 619 will be considerably greater than 626 or 650, or in some cases the parallel combination of 626 and 650.

In one embodiment the electrode is comprised of a layer of platinum and the temperature of the electrode may be characterized by monitoring the voltage drop across the series resistances 626, 619, 650. This may be done intermittently, interspersed in the delivery of the RF energy. As the electrode heats, its resistance will increase in a well-known and repeatable fashion. As the leads 626 and 650 have lower resistance and will not self-heat appreciable, the change in resistance will by primarily due to the heating of electrode 619 and variation in its resistance. Many other scenarios will be understood to those skilled in the art.

An alternate arrangement which relies on the use of a PTC for the electrode relies on the rapid change in resistance of the electrode past a particular set point which is a function of the composition of the electrode. In this configuration the tempco of the electrode is relatively small, for example, below about 40 C but above about 40 C. In this temperature range the tempco rapidly increases thereby limiting delivered power in a voltage-limited RF configuration. Many alternate embodiments will be understood by those skilled in the art.

Figure 13:
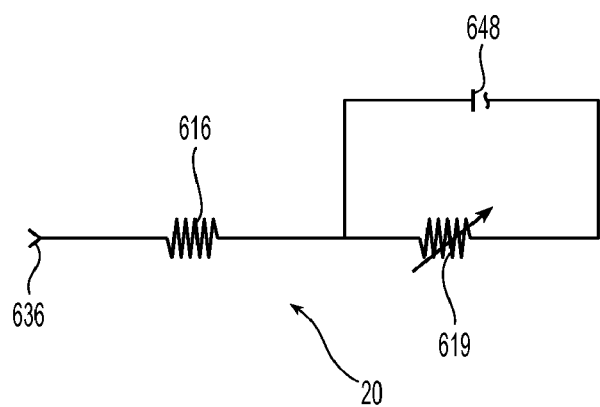
FIG. 13 illustrates an alternative configuration in which a capacitor, inductor, or both may be incorporated in the circuit from FIG. 12.

FIG. 13 illustrates an alternative configuration in which a capacitor 648, inductor (not shown), or both may be incorporated in the circuit. In one embodiment the circuit may incorporate only one source lead 621 and the inherent resonance of the circuit which will depend on the varying impedance of the electrode resistance 623.

In yet another alternative the tempco associated with a conductive ink such as the ECM CI-1036 may be used. Experimentally the ECM CI-1036 demonstrated a 0.1% increase in impedance per degree over the range of 30 C to 60 C.

Figure 16:
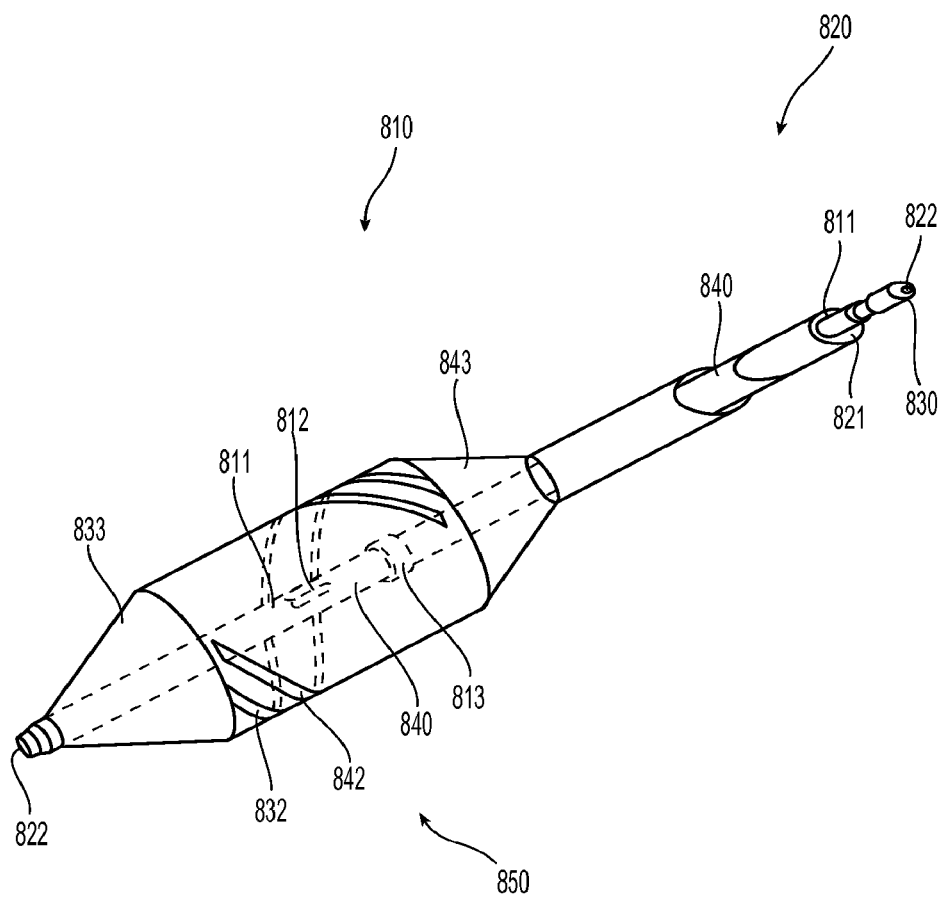
FIG. 16 illustrates a portion of an energy delivery device including a helical electrode pair on an expandable element according to another embodiment of the present disclosure.

As described above, devices capable of ablating renal nerves surrounding the renal arteries are useful in treating hypertension. The device disclosed in FIG. 16 is another embodiment of a device adapted for such purpose. The device described herein comprises a bipolar electrode pair disposed on the outer surface of an expandable structure comprised of an inflatable balloon. A bipolar electrode pair provides for both a more controlled burn and a shallower burn than a comparable monopolar electrode. The device is configured for endovascular delivery to a renal artery. Each of the individual electrodes comprising the bipolar set is in turn comprised of a unitary electrode/conductor.

Referring to FIG. 16, detailed description of the distal features of an embodiment of the device is as follows. The distal portion of a bipolar RF delivery device 810 includes an expandable section 850 including a balloon, and a catheter shaft section 820 including an inner shaft 830 and an outer shaft 840. The inner lumen of the inner shaft 830 includes a guidewire lumen 822. The annular gap between the inner and outer shafts includes an irrigation lumen 821. The outer shaft 840 also includes an irrigation outflow 812 (e.g., an irrigation port) located near its distal end such that it is disposed within the balloon. A temperature sensor 811 may be located within the balloon 850 and interconnecting leads of the temperature sensor 811 may be routed through the irrigation lumen outflow 812 and irrigation lumen 821.

Prior to assembly, a conductive material is deposited on substantially the entire inner shaft 830. A dielectric material is then deposited on the conductive material except at the distal most end of the inner shaft 830. The inner shaft 830 is then fitted within the outer shaft 840 and the two are affixed to one another such that the inner shaft 830 extends beyond the most distal portion of the outer shaft 840 and the balloon 850. The dielectric on the inner shaft 830 is deposited on at least the portions of the surface of the conductor on the inner shaft 830 that would contact irrigation fluid, thus preventing the conductive material on the inner shaft 830 from coming into contact with irrigation fluid. The distal end of the inner shaft 830, which extends distal to the outer shaft 840, is not coated with dielectric. This allows the inner shaft 830 to be in electrical communication with the inner sourced electrode as described below.

Next, the outer shaft 840 and balloon 850 are coated with an elastomeric ink, and then, subsequently, by a dielectric as described above. The conductive coating is deposited on the outer shaft 840, all or a portion of the proximal cone 843 of the balloon 850, and on the balloon 850, forming a conductive material that includes an outer sourced spiral electrode 842. This conductive material can be deposited in a unitary manner, as is described above and in the materials incorporated by reference herein. Conductive material is also deposited on the most distal section of the shaft assembly, the distal cone portion 833 of the balloon 850, and the balloon 850, forming a conductive material that includes an inner sourced electrode 832. This conductor can also be formed in a unitary manner. The conductive material that forms the inner sourced electrode can be the same material that is used for the outer sourced electrode. When the distal conductor (which includes the inner sourced electrode 832) is formed, it interfaces electrically with the conductor on the inner shaft 830 that extends distal to the balloon 850. The conductive materials can be selected such that when the conductive materials are deposited, the interface is a single layer of the same material rather than two distinct layers. The conductor and dielectric structures can be fabricated as described above. When used in bipolar mode, energy passes from one spiral electrode 832 or 842, through renal nerve tissue, to the other electrode. The electrodes 832, 842 can be used in a bipolar manner, or each electrode can be used in monopolar mode. Bipolar mode can be used if the tissue burn need not be as deep as may be needed if using a monopolar mode. Bipolar mode generally allows more control in the tissue burn. Additionally or alternatively, the electrodes 832, 842 can be used together as a single monopolar electrode (e.g., by feeding both electrodes with the same frequency and RF energy such that the electrodes appear to be one electrode).

In an alternative embodiment, the inner shaft is not coated with a conductor (or dielectric) and, instead, a wire extends through the irrigation lumen, and interfaces the conductor that includes the inner sourced electrode.

Although not shown in FIG. 16, irrigation ports as described above can be situated such that they pass through the electrode structures, sit adjacent to the electrode structures such as in the space between them or exterior to the pair, or both.

One or more radio opaque markers 813 may be affixed to the outer shaft.

In embodiments, an anesthetic solution may be introduced in conjunction with, or independent of, the irrigation fluid, to potentially reduce pain or discomfort associated with renal denervation treatment. Suitable anesthetics include lidocaine, articaine, bupivacaine, cinchocaine/dibucaine, etidocaine, levobupivacaine, lidocaine/lignocaine, mepivacaine, prilocaine, ropivacaine, trimecaine. Other possibilities include but are not limited to drugs which target neuropathic pain such as: butyl-para-aminobensoate (Butamben®), an ester local anesthetic, bupivacaine microspheres, SNX-111 (a selective calcium channel blocker), nicotinic acetylcholine receptor agonists such as ABT-594, and adrenergic blocking agents such as guanethidine or reserpine. Lidocaine is particularly suitable because it is approved for arterial use and the systemic limits are understood. In addition, lidocaine is a small molecule, which may result in faster diffusion through the artery wall. A contrast agent may be incorporated in the solution to enable visualization of the delivery of the anesthetic solution and confirmation that the targeted nerve structure has been engulfed by the solution. The contrast agent can be mixed with the anesthetic solution before the mixture is conveyed through the catheter. Examples of suitable contrast agents include those traditionally used for angiographic imaging such as the non-ionic fluoroscopic contrast agents that are iodate based (e.g., UltraVist 300).

Several factors for consideration in the delivery of an anesthetic solution as part of a renal denervation procedure include the ability to control the total dose or volume delivered and the ability to control the residence time or period the anesthetic solution remains at the treatment site while considering parameters relating to mobility, tissue density, etc. to ensure the anesthetic solution reaches the target renal nerves. The total volume delivered may vary depending on the targeted tissue and the anesthetic used. For lidocaine, the volume may be about 10 ml for a 1% solution.

Various approaches for delivery of the anesthetic solution to target nerve tissue for alleviating pain during renal denervation include, e.g., a high pressure delivery approach and/or a dwell time approach. The targeted nerve tissue may include nerve tissue in the intima, media, adventitia, and/or surrounding tissue of a renal artery. Generally, a high pressure delivery approach involves delivering anesthetic solution under relatively high pressure against the renal artery wall to cause passing within and/or through the wall via the vaso vasorum and infiltrate the targeted nerve tissue. With the dwell time approach, the anesthetic solution is maintained within the renal artery for a period of time to eventually diffuse or otherwise migrate through the vessel wall to at least partially engulf the targeted nerve tissue. Any of the aforedescribed embodiments of the energy delivery devices may be modified to deliver the anesthetic solution via the high pressure or dwell time approaches.

Figure 17:
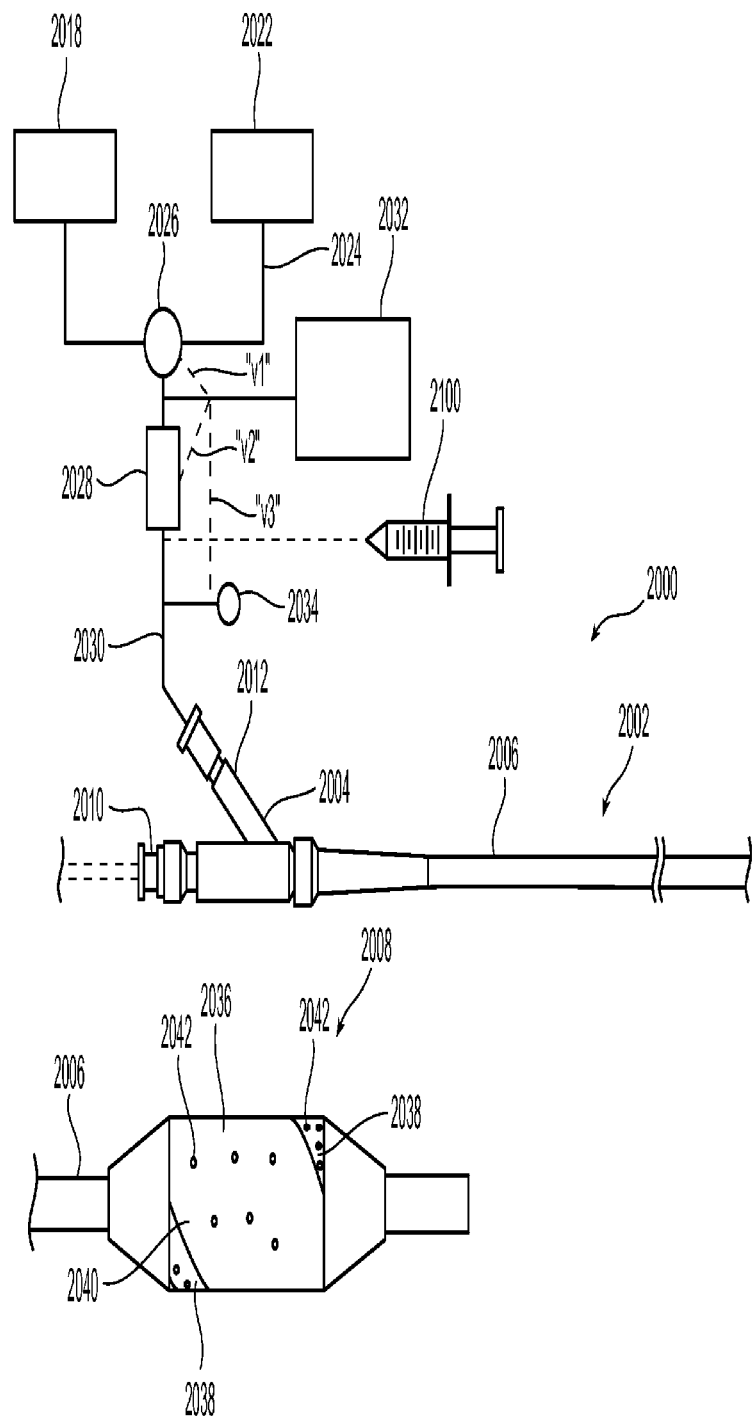
FIG. 17 is view of a system including an energy delivery device capable of delivering an anesthetic solution to tissue according to an embodiment of the present disclosure.
Figure 18:
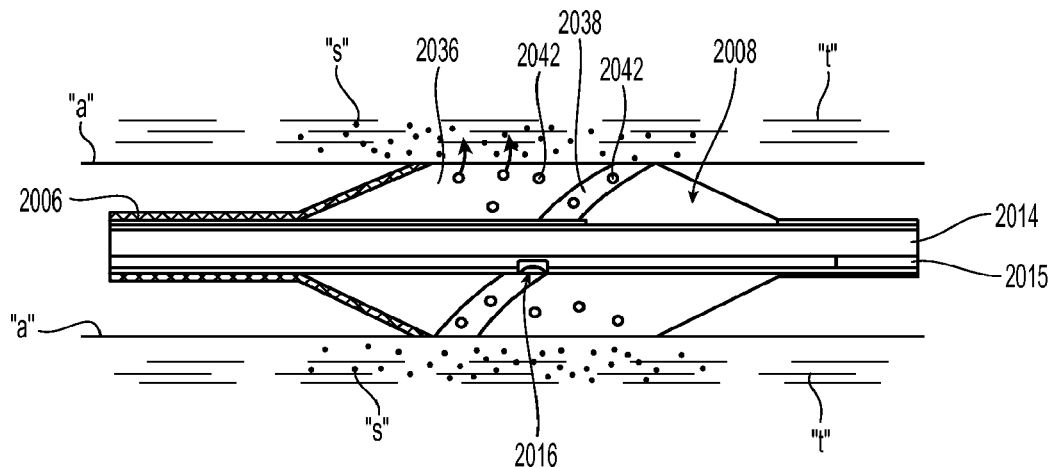
FIG. 18 is a cross-sectional view illustrating the expandable treatment member of the energy delivery device of FIG. 17 delivering an anesthetic solution through a wall of a renal artery and into the surrounding renal nerve tissue.

Referring now to FIGS. 17-18, there is illustrated an energy delivery system 2000 for delivering an anesthetic solution under high pressure to the renal vasculature (e.g., the renal artery or a renal vein), such that the solution enters the vessel wall and potentially migrate to the renal nerve structure surrounding the artery or vein. The energy delivery system 2000 includes a catheter 2002 having a catheter hub 2004, an elongate catheter member 2006 extending distally from the hub 2004 and an expandable treatment member 2008 mounted to the catheter member 2006. The elongate catheter member 2006 and the treatment member 2008 may be substantially similar to the elongate portion 12 and the expandable portion 14, respectively, of the energy delivery device 10 disclosed in connection with FIGS. 1A-2. The hub 2004 may include one or more ports for reception of a guidewire, introduction of fluids or the like. In embodiments, the catheter hub 2004 includes a guidewire port 2010 and a fluid port 2012. The guidewire port 2010 is in communication with a guidewire lumen 2014 extending through the catheter member 2006. The fluid port 2012 is in fluid communication with a fluid lumen 2015 extending through the catheter member 2006 and communicating with the treatment member 2008 through a fluid opening 2016. The fluid opening 2016 extends through the wall of the catheter member 2006 and communicates with an interior portion of the treatment member 2008.

The energy delivery system 2000 further includes an irrigation or inflation source 2018 and associated irrigation fluid line 2020. The irrigation source 2018 includes fluids for expanding the treatment member 2008 and/or for cooling tissue and/or for cooling the conductive material on the treatment member 2008. Any of the aforementioned irrigation fluids may be utilized.

The energy delivery device 2000 further includes a source of anesthetic solution 2022 and associated anesthetic fluid line 2024. The anesthetic source 2022 may include any of the anesthetic solutions mentioned hereinabove or other anesthetic solutions.

The energy delivery system 2000 may further include a valve 2026 which is in line with the irrigation fluid line 2020 and the anesthetic fluid line 2024 to permit selective infusion of either the irrigation fluid or the anesthetic solution. The valve 2026 may be manually operated or may be controlled via automation (e.g., programmable) to switch between an irrigation mode for supplying irrigation fluids from the irrigation source 2018 and an anesthetic mode for supplying the anesthetic solution from the anesthetic source 2022. A pump 2028 may be in fluid communication with the valve 2026 to deliver the irrigation fluid or the anesthetic solution under pressure to the fluid lumen 2012 via a supply line 2030.

The energy delivery system 2000 may also include a controller, identified schematically as reference numeral 2032, with associated logic, software or circuitry for controlling operation of the pump 2028 and/or the valve 2026. The software may contain at least one program for automated operation of the pump 2028 and/or the valve 2026 and/or may operate in response to various parameters detected during operation. For example, a sensor 2034 may be in communication with the feed line 2030 extending from the pump 2028 to the fluid port 2012 of the catheter hub 2004 to detect flow rate (e.g., a flow rate sensor) or pressure associated (e.g., a pressure sensor or transducer) with the irrigation fluid or anesthetic solution delivered to the expandable treatment member 2008. The activity of the pump 2028 (e.g., an increase or decrease in pump speed, output or flow rate) may be controlled by the controller 2032 based at least in part on parameters detected by the sensor 2034. Signals transmitted between the controller 2032 and the valve 2026, the pump 2028 and the sensor 2034 are represented as signals "v1", "v2", "v3", respectively.

The expandable treatment member 2008 may be any of the expandable portions described hereinabove. In embodiments, the treatment member 2008 includes a balloon or inflatable element 2036, a helical electrode 2038 on the outer surface of the inflatable element 2036 for delivering energy to the renal nerve tissue and non-conductive segment or material 2040 surrounding the helical electrode 2038. The treatment member 2008 further includes a plurality of apertures 2042 defined in the inflatable element 2036 and/or the helical electrode 2038. In FIGS. 17 and 18, the apertures 2042 are present in both the helical electrode 2038 and the non-conductive segment 2040 of the inflatable element 2036 for illustrative purposes. The apertures 2042 may have pore sizes ranging from about 0.5 mil to about 10 mil. The pore size, pore density and the thickness of the inflatable element 2036 may be selected to deliver the anesthetic solution at a pressure sufficient to pass through the renal artery wall for dispersion into the renal artery wall and possibly to surrounding renal nerves. The pressure of the anesthetic solution may vary, but in embodiments, a range of pressure within the inflatable element 2036 is between about 1 atm to about 4 atm. When desired, a relatively high pressure may be used to deliver anesthetic solution at a velocity sufficient to cause the solution to enter the renal artery and ultimately migrate to targeted nerves, including those in the media, adventitia, or surrounding tissue.

In operation, with reference to FIG. 18, the treatment member 2008 is positioned at the targeted location within the renal artery "a" or other renal vasculature. The anesthetic solution is then delivered by positioning the valve 2026 either manually or automatically via the controller 2032, to the anesthetic mode. The pump 2028 is activated to deliver the anesthetic solution to the fluid port 2012 through the inflation lumen 2015 and within the interior of the inflatable element 2036 for delivery through the apertures 2042 under high pressure. The anesthetic solution "s" delivered within the pressure range identified hereinabove will enter and pass within and/or through the renal artery wall "a" and migrate to the renal nerve fibers or tissue "t" via the vasculature in the vessel wall. During application of the anesthetic solution "s", the pressure within the inflatable element 2036 or inflation lumen 2015 may be monitored with the sensor 2034, which sends a signal back to the controller 2032. For instance, in the event the sensed pressure is below a threshold value potentially indicating that the anesthetic solution "s" is being delivered from the apertures 2042 at a relatively low pressure where diffusion is the primary manner in which it passes within and/or through the vessel wall, the pump or flow rate may be increased to increase the flow rate through the vessel to enhance the passage of the anesthetic within and/or through the blood vessels in the vessel wall. Similarly, if the sensed pressure is above a threshold value, flow rate delivered by the pump 2028 may be decreased to an acceptable range.

Once the renal nerves are desensitized by the anesthetic solution "s", the valve 2026 can be switched to the irrigation mode and the controller 2032 activated to introduce irrigation and/or inflation fluids through the inflation lumen 2015 and within the inflatable element 2036. In the irrigation mode, the flow rate and pressure may be reduced relative to the anesthetic mode to a pressure, e.g., below 1 atm. The inflatable element 2036 expands to position the helical electrode 2038 in apposition with the wall of the renal artery "a". The system is energized and energy is delivered through the helical electrode 2038 to treat and/or denervate the renal nerves. The irrigation fluid cools the electrode 2038 and surrounding tissue as described hereinabove.

If during treatment, it is determined that another injection of anesthetic solution "s" is warranted, the irrigation fluid within the inflatable element 2036 may be drained either passively or actively from the inflatable element 2036, and the anesthetic fluid delivered directly to the uninflated inflatable element 2036 for delivery to the nerve tissues through the apertures 2042. In some embodiments, the anesthetic solution "s" may be prefilled within the inflatable element 2036, and used to purge the system 2000 prior to use. This may present a more efficient and faster method for delivery of the anesthetic solution "s".

In embodiments, the helical electrode 2042 may be used to enhance the delivery of the anesthetic solution "s" through electrophoresis. For example, the helical electrode 2042 can be used to deliver a low current high voltage creating a charge gradient across the tissue, which increases the infusion rate of ionic anesthetic solutions "s" through the wall and into the nerves. In some embodiments, the generator associated with the controller 2032 can have two settings. The first setting can be for the delivery of a high voltage low current signal to the electrode 2038 during delivery of the anesthetic solution "s" to establish the electrophoretic environment. The second setting can be for the delivery of RF energy for nerve ablation. The use of electrophoresis to improve infusion of anesthesia into the tissue can be used with any of the single electrode helical electrode configurations described in FIGS. 1-15 and 17-18 and/or the double electrode configuration of FIG. 16. In embodiments, the first setting of the generator also may be utilized to deliver non-RF voltage to excite the surrounding renal nerves. When the patient indicates to the clinician that the patient no longer feels the excited nerves, the clinician is apprised that the nerve tissue may be sufficiently anesthetized for the denervation treatment.

In embodiments, the source of anesthetic solution 2022 and the pump 2028 may be replaced with a syringe 2100 containing the anesthetic solution "s" (FIG. 17). The syringe 2100 may be introducible within or coupled to the fluid port 2012 of the catheter hub 2004 and delivered to the inflation lumen 2015 and the inflatable element 2036 of the treatment member 2008 for dispensing through the apertures 2042. The syringe 2100 may be manually activated. The flow of the anesthetic solution "s" may be moderated by the clinician via monitoring of the pressure via the sensor 2034 to provide delivery of the anesthetic solution "s" at the desired flow rate and high pressure sufficient to pass within and/or through the wall of the renal artery "a" and migrate to the targeted renal nerve tissue "t". The syringe 2100 may have gradations to assist the clinician in determining the volume of anesthetic solution "s" delivered to the inflatable member 2036. Additionally or in the alternative, the syringe 2100 may be filled with a predetermined volume of anesthetic solution "s" corresponding to a maximum volume intended for use during the treatment. Other fluid displacement mechanisms both manual and automated for delivering the anesthetic solution "s" are also within the scope of this disclosure.

As indicated hereinabove, in certain embodiments, instead of, or in addition to, the high pressure delivery of anesthetic solution to the renal nerves, a dwell-time approach may be utilized for delivery of anesthetic solution to the renal nerves. In accordance with this approach, the anesthetic solution is caused to dwell for a sufficient period of time at the treatment site such that the anesthesia solution has time to passively diffuse or otherwise move through the wall of the renal vasculature, e.g., the renal artery "a" or a renal vein. Increasing the dwell time of anesthetic solution at the treatment site can effectively increase the volume of delivered anesthesia that passes within and/or through the wall of the renal artery. This can, for example, result in delivery of an effective amount of anesthetic while using only a small portion of the overall systemic dose of the anesthetic solution.

In embodiments, the anesthetic solution may incorporate or be infused with microbeads. For example, microbeads can be saturated in an anesthetic such as lidocaine. The saturated microbeads can be mixed with saline to form the anesthetic solution and the solution can be delivered to the inflatable member 2036. The anesthetic solution will leave the microbeads as the microbeads migrate through the vessel wall of the renal artery "a" acting as a localized drug source delivering the anesthetic for a predetermined period of time during their migration and when at rest. This may increase the amount of time the anesthetic or drug is active in the area. This can facilitate the use of less anesthetic solution and allow for the anesthetic to be active for a longer period of time as compared to an injected drug, which gets removed by the lymphatics.

Figure 19:
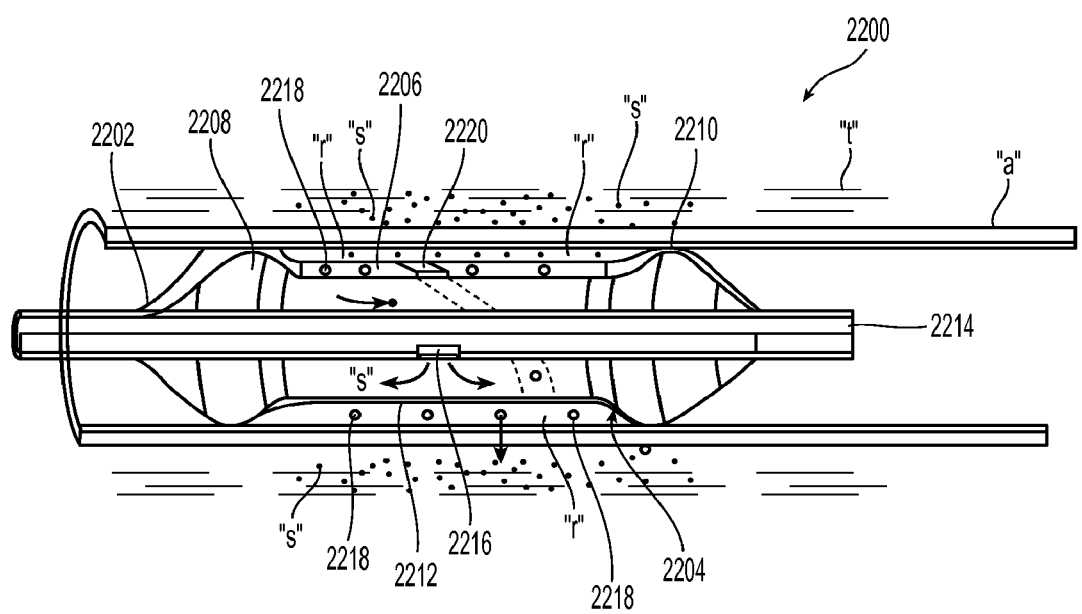
FIG. 19 is a view illustrating an expandable treatment member of an energy delivery device adapted to deliver anesthetic solution through the wall of the renal artery to the surrounding renal nerve tissue according to an embodiment of the present disclosure.

In the alternative, the dwell time of anesthesia delivery may be increased by altering the rate of delivery of the anesthetic solution into the inflatable element of the treatment member thereby slowing the infusion rate into the renal artery. One procedure using an anesthetic solution containing lidocaine for treating renal arteries prior to an RF ablation for the treatment of hypertension includes a slow infusion of 2-4 ml of a 1% lidocaine solution (20-40 mg lidocaine) with an upper limit of a bolus 10 ml (100 mg lidocaine). Referring now to FIG. 19, one embodiment of an energy delivery system 2200 adapted for delivering an anesthetic solution through a dwell-time approach in conjunction with energy delivery is illustrated. The configuration of the catheter 2202 of the system 2200 is substantially similar to the embodiment of FIGS. 8 and 9, and reference is made thereto for particulars of the catheter member 2202 and the expandable treatment member 2204. The system 2200 may incorporate features of the system 2000 discussed in connection with FIGS. 17 and 18 for providing automated control of infusion rate, pressure and/or delivery volume. The treatment member 2204 includes an inflatable element 2206 having enlarged proximal and distal occluding end segments 2208, 2210 and an intermediate or central segment 2212 disposed between the proximal and distal end segments 2208, 2210. In embodiments, the inflatable element 2206 is a single balloon member. The enlarged end segments 2208, 2210 define a greater cross-sectional dimension or diameter than the intermediate segment 2212 when in an at least partially expanded condition as shown in FIG. 19, thereby defining a general dumbbell shape to the expanded inflatable element 2206. In accordance with this embodiment, the spacing defined between the intermediate segment 2212 of the inflatable element 2206 and the vessel wall of the renal artery "a" provides a reservoir "r" for receiving the anesthetic solution "s". Thus, upon expansion of the inflatable element 2206, the end segments 2208, 2210 engage the interior wall surface of the renal artery "a" while the intermediate segment 2212 is in a spaced relation from the interior wall surface. The end segments 2208, 2210 are dimensioned to substantially occlude the interior of the renal artery "a" thereby enclosing the reservoir "r". Anesthetic solution "s" is introduced within the irrigation lumen 2214 of the catheter member 2202 and delivered through the irrigation port 2216 under relatively low pressure, e.g., less than about 2 atm. or less than about 1 atm. The anesthetic solution "s" passes through the apertures 2218 within the inflatable element 2200 and/or in the helical electrode 2220. Due to the reservoir holding capacity, the anesthetic solution "s" remains in contact with the vessel wall of the renal artery "a". Over time, the anesthetic solution "s" diffuses through the wall and into the surrounding renal nerve tissue "t" so that the solution has its desired anesthetic effect. In some implementations, the anesthetic solution "s" delivered to the reservoir "r" can be removed after a predetermined treatment period via aspiration through the irrigation port 2216 to minimize the amount of anesthetic remaining in the patient's system. Irrigation fluid may then be delivered to the inflatable element 2206 and the system energized such that the electrode 2220 delivers energy to denervate the nerve fibers. The irrigation fluid cools the electrode 2220 and/or the surrounding tissue.

Figure 20:
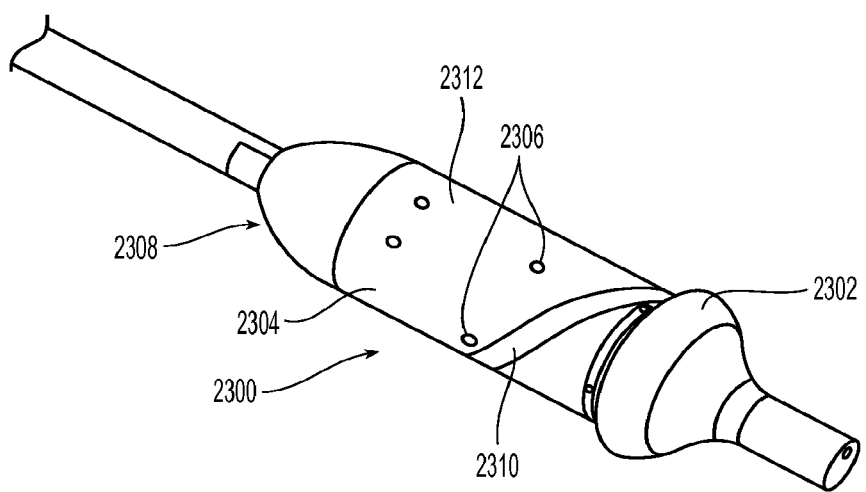
FIG. 20 is a perspective view of an expandable treatment member of an energy delivery device adapted to deliver anesthetic solution according to an embodiment of the present disclosure.

FIG. 20 illustrates a variation of the treatment member of FIG. 19 where the inflatable element 2300 includes an enlarged distal end region 2302 while the main section 2304 of the inflatable element 2300 is of a constant smaller cross-sectional dimension or diameter when in the at least partially expanded condition of the inflatable element 2300. With this arrangement, a more distal region of the renal artery "a" is occluded and anesthetic solution "s" is delivered through apertures 2306 in the main section 2304 to the renal artery and the renal nerves. Although the reservoir is open adjacent the proximal end 2308 of the inflatable element 2300, the flow rate of the anesthetic solution "s" may be controlled to ensure a sufficient dwell time or period is achieved for the anesthetic solution "s" to pass from the reservoir to the renal nerves. In an alternative use, the proximal end 2308 of the inflatable element 2300 may occlude a vessel wall due to the geometry of the vasculature in which it is positioned to substantially enclose the reservoir. For example, the proximal end 2306 may be positioned within a more narrow area of the renal vasculature, which, upon expansion will engage and at least partially occlude the wall to enclose the reservoir. In another approach, the proximal end 2306 may be positioned adjacent a curve or bend in the renal vasculature whereby the proximal end 2306 engages the curve to assist in enclosing the reservoir. As a further alternative, the proximal end 2306 of the inflatable element 2300 may be enlarged while the rest of the main section 2304 of the inflatable element 2300 including the distal end region is of constant dimension or diameter. Although the apertures 2306 are shown in the non-conductive segment 2312 of the inflatable element 2300, the apertures 2306 may extend through the helical electrode 2310 or through both the electrode 2310 and the non-conductive segment 2312 of the main section 2304.

Figure 21:
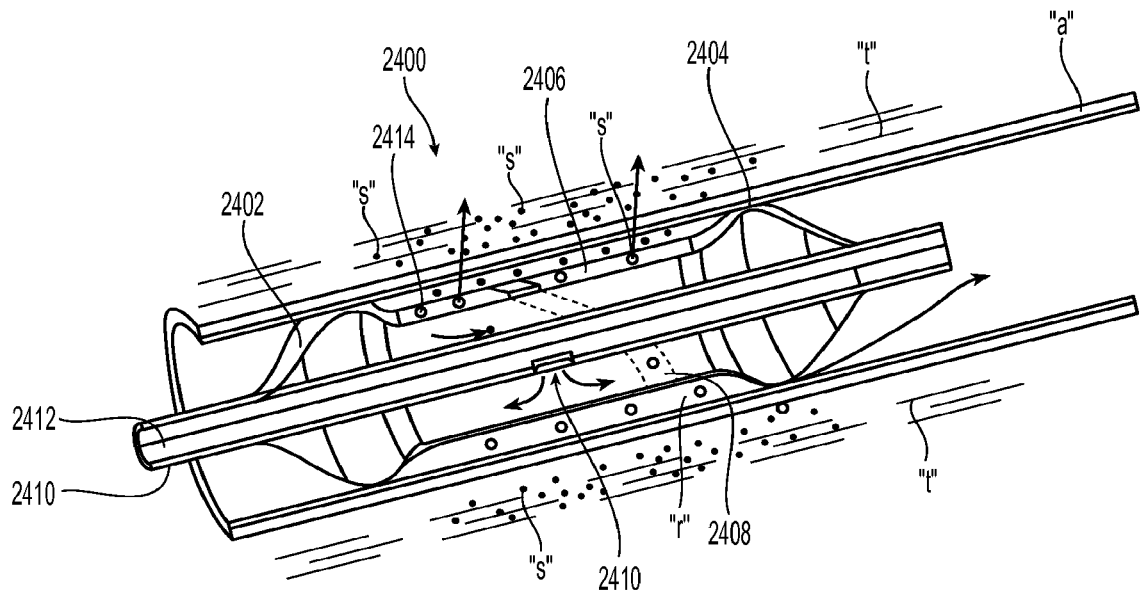
FIGS. 21-22 are views illustrating an expandable treatment member of an energy delivery device for delivering anesthetic solution through the wall of the renal artery to the surrounding renal nerve tissue according to an embodiment of the present disclosure.
Figure 22:
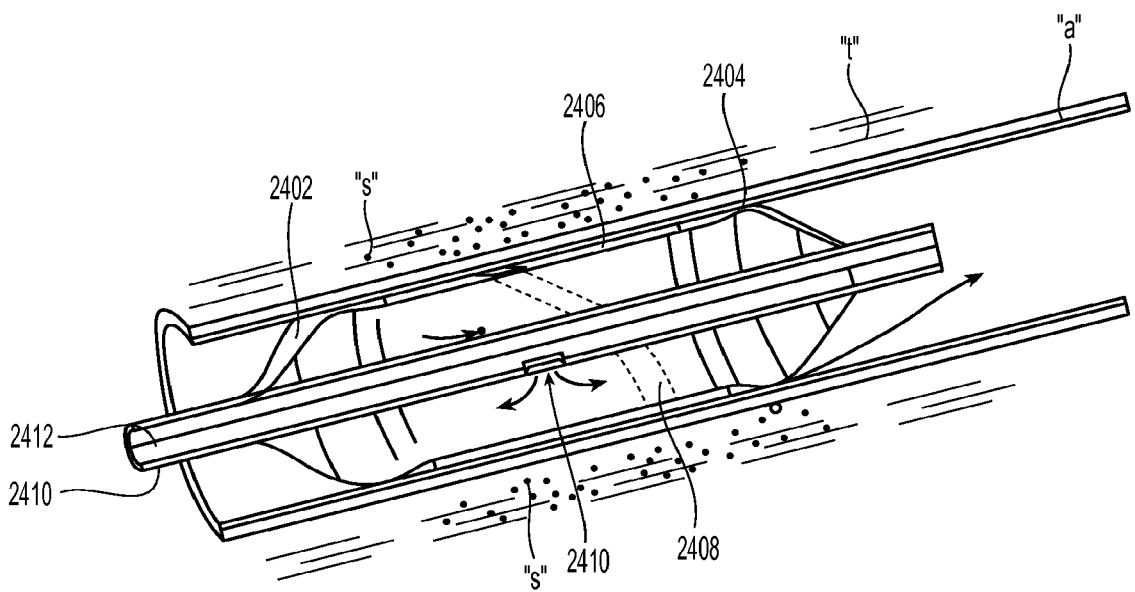

FIGS. 21-22 illustrate an alternate embodiment of the expandable treatment member of FIGS. 8, 9 and 19. In accordance with this embodiment, an inflatable element 2400 is dimensioned to transition between at least two conditions depending on the fluid operational pressure within the interior of the inflatable element 2400. At a first operational state or pressure depicted in FIG. 21, the inflatable element 2400 assumes the general "dumbbell" orientation with the proximal and distal occluding end segments 2402, 2404 defining a greater cross-sectional dimension or diameter than the intermediate segment 2406. At a second operational state or pressure greater than the first operational state depicted in FIG. 22, the intermediate segment 2406 expands to generally approximate the dimension or diameter of the proximal and distal end segments 2402, 2404. The proximal and distal end segments 2402, 2404 maintain substantially the same dimension or diameter exhibited in the first operational state. In embodiments, the inflation element 2400 is a single balloon member where the intermediate segment 2406 may be fabricated from a more conformable material than the end segments 2402, 2404 to permit greater expansion of the intermediate segment 2406 when subjected to the increase pressure of the second operational state. In other embodiments, the end segments 2402, 2404 could incorporate stiffening material or elements, such as polymeric strands, braids, woven materials, splines, or the like. The stiffening elements would be fabricated from a material which will not interfere with the functioning of the helical electrode 2408.

In operation, a catheter member 2410 is advanced to position the inflatable element 2400 within the renal vasculature at the targeted site. The inflatable element 2400 is inflated to assume the first state or condition with the proximal and distal end segments 2402, 2404 engaging and at least partially occluding the vessel wall with the intermediate segment 2406 spaced from the wall to define the annular reservoir "r" discussed hereinabove and shown in FIG. 21. The anesthetic solution "s" is introduced within the interior of the inflatable element 2400 and communicates through the fluid port 2410 in fluid communication with the fluid lumen 2412 and out the apertures 2414 to at least partially fill the reservoir "r". The anesthetic solution 's" will eventually diffuse through the wall of the renal artery "a" distributing within the renal nerves "t" in the tunica intima, tunica media, and adventitia to anesthetize the tissue. Thereafter, the inflatable element 2400 may be expanded to its second operational state through the introduction of the irrigation fluid at, e.g., a greater pressure and/or flow rate, whereby the intermediate segment 2406 expands to contact the vessel wall as depicted in FIG. 22. In the second state, the helical electrode 2408 is in apposition with the vessel wall. Energy can be delivered to the helical electrode 2408 to provide the desired treatment.

Figure 23:
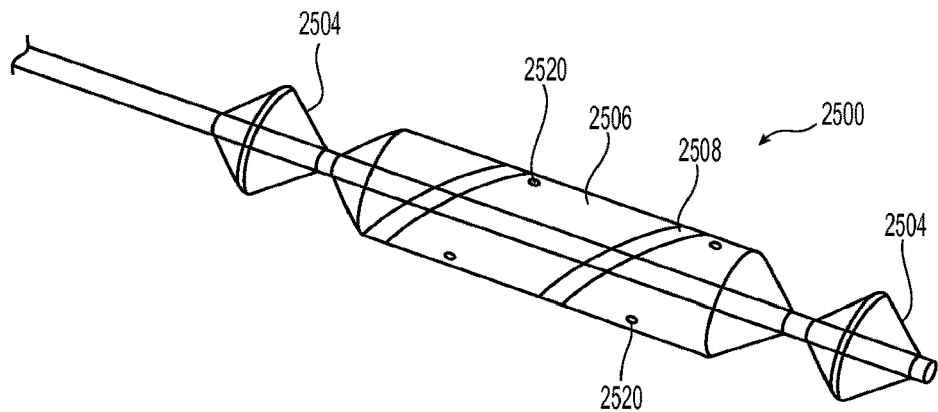
FIGS. 23-25 are views of an expandable treatment member including proximal and distal occluding elements and a central inflatable element for delivering anesthetic solution according to an embodiment of the present disclosure.
Figure 24:
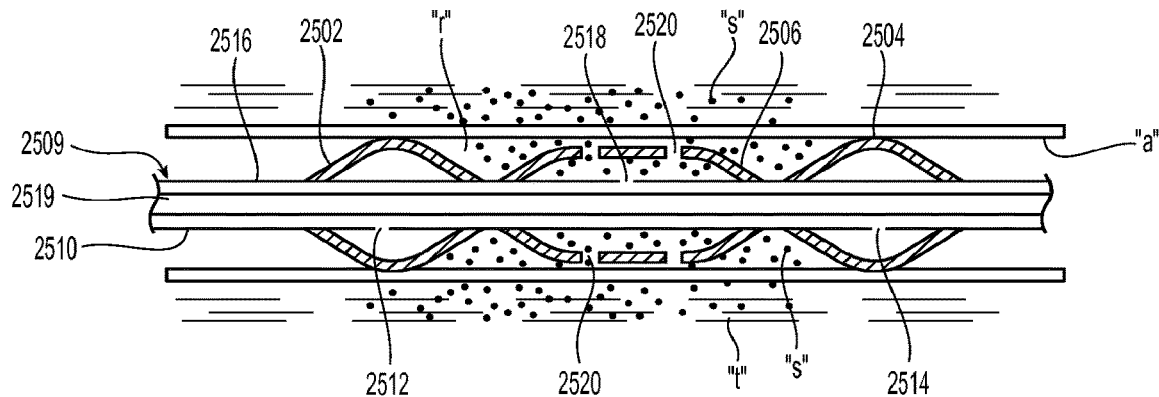
Figure 25:
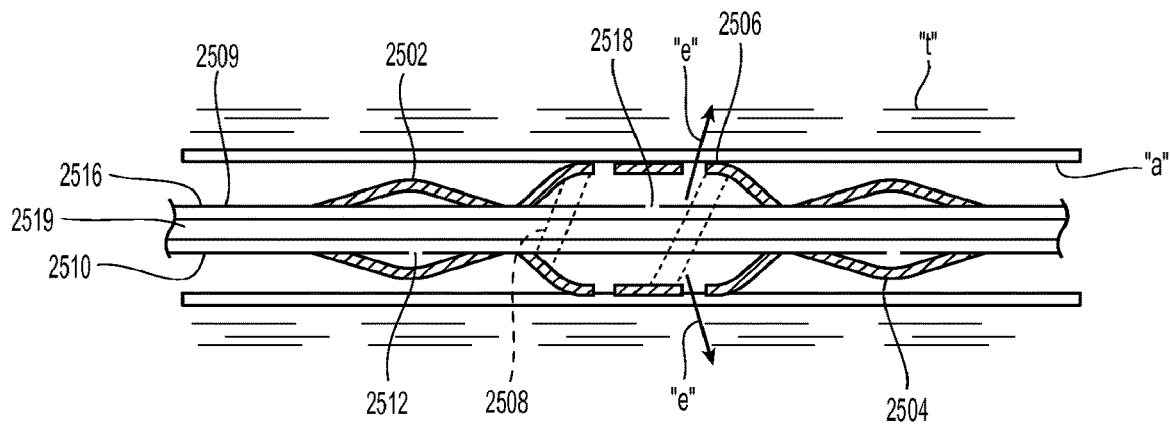

FIGS. 23-25 illustrate an embodiment of the energy delivery system where the treatment member 2500 includes proximal and distal occluding balloon elements 2502, 2504 with an intermediate or central balloon or inflation element 2506 disposed therebetween. The central balloon element 2506 is a treatment balloon and incorporates the helical electrode 2508 to treat the tissue in the aforementioned manner. The proximal and distal balloon elements 2502, 2504 may be expandable independent of the central balloon element 2506 to occlude the renal vessel and form the reservoir "r" for accommodating the anesthetic solution "s" as shown in FIG. 24. In embodiments, the catheter member 2509 may include a first lumen 2510 (shown schematically) in fluid communication with each of the balloon elements 2502, 2504 through fluid ports 2512, 2514, respectively. With this arrangement, the proximal and distal inflation elements 2502, 2504 are simultaneously inflated or deflated. In the alternative, proximal and distal balloon elements 2502, 2504 may be isolated from one another and inflated independent from each other by provision of an additional lumen (not shown). The catheter member 2509 may include a second lumen 2516 (shown schematically) in fluid communication with the central balloon element 2506 through fluid opening 2518. In embodiments, the catheter member may include a third lumen 2519 for receiving the guidewire. The central balloon element 2506 includes a plurality of apertures 2520 extending through its wall for delivering the anesthetic solution or the irrigation fluid. The apertures 2520 may also extend through the helical electrode 2508.

In operation, the expandable treatment member 2500 is positioned at the desired location within the renal artery "a". The proximal and distal occluding balloon elements 2502, 2504 are simultaneously inflated with the irrigation fluid to occlude the renal artery at upstream and downstream locations as shown in FIG. 24. The anesthetic solution "s" may be delivered through the second lumen 2516 at a first pressure and into the central balloon element 2506 via the fluid opening 2518. The central balloon element 2506 may be at least partially inflated while the anesthetic solution "s" flows through the apertures 2520 within the central balloon element 2506 and into the reservoir "r". For example, infusion of the anesthetic solution "s" through the central balloon element 2506 can be controlled to limit expansion of the central balloon element 2506 such that the annular space of the reservoir "r" is maintained to accommodate the anesthetic solution "s". After diffusion of the anesthetic solution "s" through the renal artery "a" and the renal nerve tissue "t", the proximal and distal balloon elements 2502, 2504 may be deflated and the central balloon element 2506 further expanded via introduction of irrigation fluid to position the helical electrode 2508 in apposition with the wall of the renal artery "a" as depicted in FIG. 25. The helical electrode 2508 is activated to transmit energy to denervate the targeted nerve tissue "t". In the alternative, the proximal and distal balloon elements 2502, 2504 may remain in their expanded state during treatment with the electrode 2508.

Figure 26:
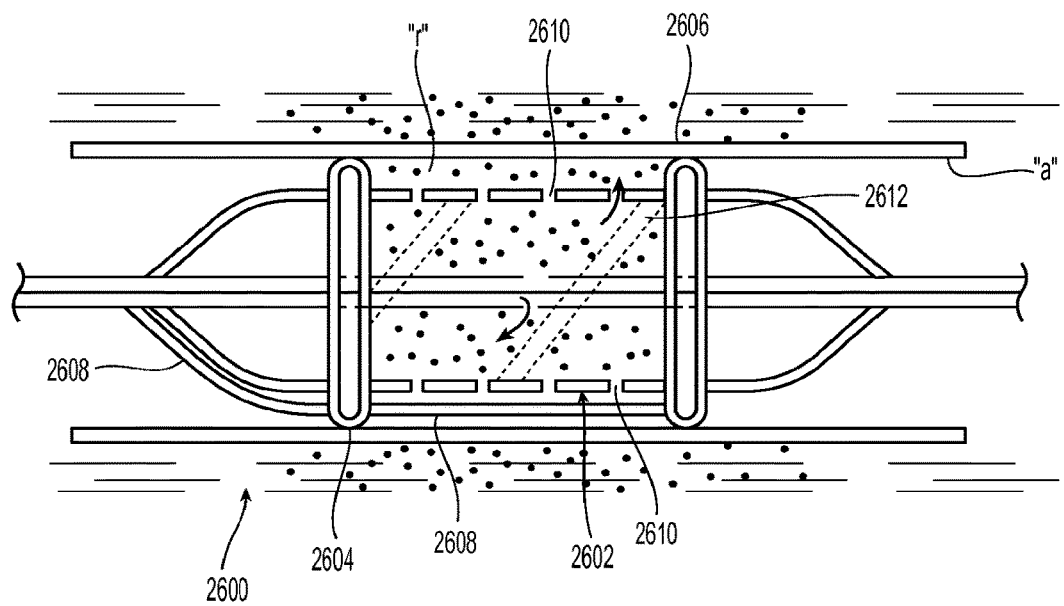
FIG. 26 is a view of an expandable treatment member for delivering anesthetic solution according to an embodiment of the present disclosure.

FIG. 26 illustrates an alternate arrangement of the treatment member of FIGS. 23-25. In this embodiment, the treatment member 2600 includes central or main inflation element 2602 of generally cylindrical configuration and proximal and distal axially spaced inflation elements 2604, 2606. In embodiments, the inflation elements 2602, 2604, 2606 are individual balloon members. The proximal and distal axially spaced inflation elements 2604, 2606 may be toroidal or generally donut shaped and mounted about, or directly to, the proximal and distal ends of the main inflation element 2602, i.e., about the outer surface of the main inflation element. The first and second axial inflation elements 2604, 2606 may be in fluid communication with the irrigation fluid via tubing, identified schematically as reference numeral 2608, which may at least partially extend along the exterior of the main inflation element 2602. The proximal and distal axially spaced inflation elements 2604, 2606 are expandable to occlude the renal artery "a" and enclose the reservoir "r" defined between the at least partially inflated main inflation element 2602 and the wall of the renal artery "a". Anesthetic solution "s" is passed through the apertures 2610 of the main inflation element 2602 for diffusion through the wall of the renal artery "a" to engulf the targeted renal nerve tissue. Subsequent to the anesthetic treatment, the proximal and distal axially spaced inflation elements 2604, 2606 may be deflated and the main inflation element 2602 inflated to position the electrode 2612 in apposition with the renal artery "a" for treatment of the renal nerve tissue "t".

Figure 27:
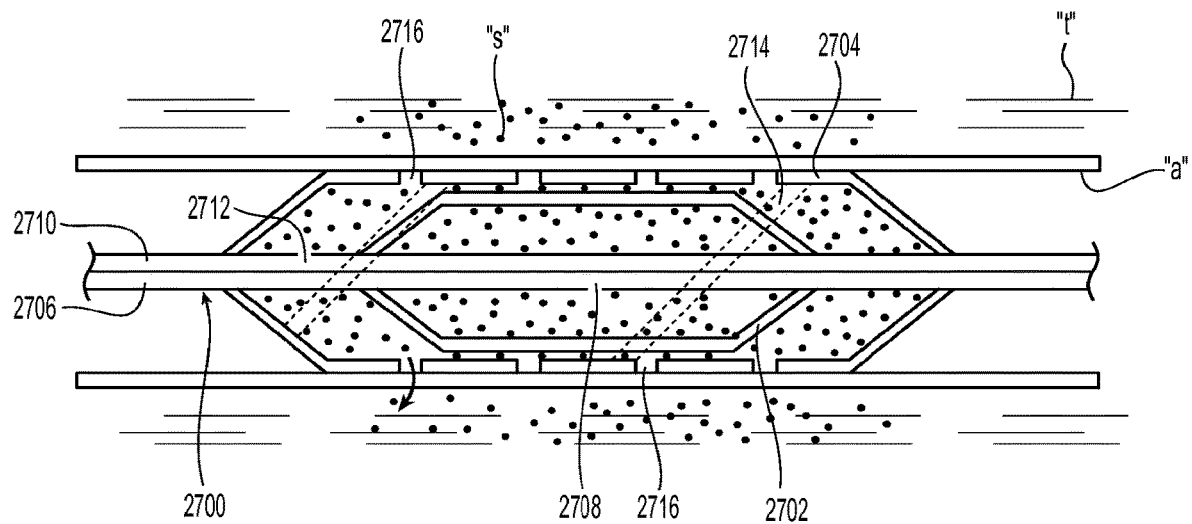
FIG. 27 is a view of an expandable element including coaxially mounted inflatable elements for delivering anesthetic solution according to an embodiment of the present disclosure.

FIG. 27 illustrates another embodiment of the energy delivery device. In accordance with this embodiment, elongate member 2700 includes first inner balloon or inflation element 2702 mounted adjacent the distal end thereof and second outer balloon or inflation element 2704 coaxially mounted about the first inner inflation element 2702. The elongate member 2700 includes a first lumen 2706 in fluid communication with the first inner inflation element 2702 through a first port 2708 within the wall of the elongate member 2700. The elongate member 2700 includes a second lumen 2710 in fluid communication with the second outer inflation element 2704 through a second port 2712 within the wall of the elongate member 2700 external of the first inflation element 2702. The second outer inflation element 2704 includes the helical electrode 2714 for treatment of tissue and incorporates the apertures 2716 through its wall for delivery of anesthetic solution. The first inner inflation element 2702 is devoid of apertures to define a fully enclosed volume.

In use, the first inflation element 2702 is at least partially inflated or fully inflated through introduction of irrigation fluids through the first lumen 2706 and out the first port 2708. The second inflation element 2704 is inflated with, e.g., the anesthetic solution "s" through introduction of the solution through the second lumen 2710 and the second port 2712. The anesthetic solution "s" fills the space or reservoir defined between the inner wall of the second inflation element 2704 and the outer wall of the first inflation element 2702. The anesthetic solution "s" passes through the apertures 2716 for delivery within and/or through the wall of the renal artery "a" into the nerve structure "t". In embodiments, the first inflation element 2702 may be fully expanded to the position depicted in FIG. 27 with only a small gap or space defined between the first inflation element 2702 and the second inflation element 2704. The gap receives the anesthetic solution "s" or the irrigation fluid. In this condition of the first inflation element 2702, the second inflation element 2704 may be pressed against the wall of the renal artery "a" by the first inflation element 2702 thereby causing contact of the helical electrode 2714 with the wall. In embodiments, a volume of anesthetic solution "s" is disposed between the small gap between the first and second inflation elements 2702, 2704 for dispersion through the apertures 2716 as depicted in FIG. 27. In some embodiments, the first inflation element 2702 may be only partially expanded and the second inflation element 2704 is maintained at full expansion via the introduction of the anesthetic solution "s" to position the electrode 2714 adjacent the renal artery during the anesthetic delivery.

Subsequent to the treatment with the anesthetic solution "s", the irrigation fluid is introduced through the second lumen 2710 and into the interior volume of the second inflation element 2704. The irrigation fluids pass through the apertures 2716 to cool the electrode 2714 and/or surrounding tissue. The first inner inflation element 2702 may be inflated/deflated to any predetermined inflation state during introduction of the anesthetic solution "s" or the irrigation fluid within the second inflation element 2704. The independent inflation of the first inflation element 2702 to maintain apposition of the electrode 2714 against the vessel wall allows the flow rate of anesthetic and/or the irrigation fluid to be independent of maintenance of the apposition of the electrode 2714 against wall. Additionally, full inflation of the first inner inflation element 2702 may reduce the volume and/or flow rate of anesthetic solution "s" or irrigation fluid required to be delivered while maintaining the electrode(s) 2714 in contact with the vessel wall.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An energy delivery system for delivering electrical energy to tissue, the energy delivery system comprising:
an elongate catheter member defining a longitudinal axis and dimensioned for passage within a body vessel; a treatment member mounted to the elongate catheter member, the treatment member comprising a proximal occluding element, a distal occluding element, and an intermediate inflation element disposed between the proximal occluding element and the distal occluding element, the intermediate inflation element comprising an electrode configured to deliver electrical energy to at least nerve tissue associated with the body vessel to cause at least partial denervation thereof;
a source of an irrigation fluid; and
a source of an anesthetic solution,
wherein the energy delivery system comprises a first configuration in which the source of the irrigation fluid is fluidly connected with both the proximal occluding element and the distal occluding element, and a second configuration in which the source of the anesthetic solution is fluidly connected with the intermediate inflation element;
wherein the proximal occluding element and the distal occluding element are fluidically coupled with each other and configured to be inflated simultaneously; and
wherein the intermediate inflation element is fluidically isolated from each of the proximal occluding element and the distal occluding element.

2. The energy delivery system according to claim 1, the elongate catheter member defining a first lumen and a second lumen, wherein in the first configuration, the first lumen fluidically connects the source of the irrigation fluid with the proximal occluding element and the distal occluding element, and in the second configuration, the second lumen fluidically connects the source of the anesthetic solution and the intermediate inflation element.

3. The energy delivery system according to claim 1, wherein the intermediate inflation element comprises a plurality of apertures.

4. The energy delivery system according to claim 1, wherein the energy delivery system is configurable such that the first configuration and the second configuration simultaneously exist.

5. The energy delivery system according to claim 4, wherein in the first configuration, the proximal occluding element and the distal occluding element are each expanded a first distance from a reference axis, and in the second configuration, the intermediate inflation element is expanded a second distance from the reference axis that is less than the first distance.

6. The energy delivery system according to claim 1, wherein in the first configuration, the proximal occluding element and the distal occluding element are each expanded a first distance from a reference axis, and wherein in the second configuration, the intermediate inflation element is expanded a second distance from the reference axis that is less than the first distance.

7. The energy delivery system according to claim 6, wherein the energy delivery system comprises a third configuration in which the source of the irrigation fluid is fluidly connected with the intermediate inflation element.

8. The energy delivery system according to claim 7, wherein in the third configuration, the intermediate inflation element is expanded a distance from the reference axis that is greater than the second distance.

* * * * *